(12) United States Patent
Meng et al.

(10) Patent No.: US 7,271,274 B2
(45) Date of Patent: Sep. 18, 2007

(54) PHENOLIC ANTIOXIDANTS FOR THE TREATMENT OF DISORDERS INCLUDING ARTHRITIS, ASTHMA AND CORONARY ARTERY DISEASE

(75) Inventors: Charles Q. Meng, Duluth, GA (US); M. David Weingarten, Cumming, GA (US)

(73) Assignee: AhteroGenics, Inc., Alpharetta, GA (US)

( * ) Notice: Subject to any disclaimer, the term of this patent is extended or adjusted under 35 U.S.C. 154(b) by 0 days.

(21) Appl. No.: 11/111,196

(22) Filed: Apr. 20, 2005

(65) Prior Publication Data

US 2006/0020038 A1 Jan. 26, 2006

Related U.S. Application Data

(60) Provisional application No. 60/600,029, filed on Aug. 9, 2004, provisional application No. 60/564,043, filed on Apr. 20, 2004.

(51) Int. Cl.
*C07D 317/10* (2006.01)
*A61K 31/335* (2006.01)
*C07C 309/00* (2006.01)

(52) U.S. Cl. ............... 549/449; 549/450; 549/453; 514/467

(58) Field of Classification Search ......... 514/562, 514/467, 618, 712; 564/162; 562/442; 568/47; 549/449, 453, 450
See application file for complete search history.

(56) References Cited

U.S. PATENT DOCUMENTS

| | | | |
|---|---|---|---|
| 4,029,812 A | 6/1977 | Wagner et al. | |
| 4,076,841 A | 2/1978 | Wagner et al. | |
| 4,078,084 A | 3/1978 | Wagner et al. | |
| 4,752,616 A | 6/1988 | Hall et al. | |
| 4,954,514 A | 9/1990 | Kita et al. | |
| 5,155,250 A | 10/1992 | Parker et al. | |
| 5,206,247 A | 4/1993 | Regnier et al. | |
| 5,262,439 A | 11/1993 | Parthasarathy et al. | |
| 5,608,095 A | 3/1997 | Parker et al. | |
| 5,627,205 A | 5/1997 | Regnier et al. | |
| 5,750,351 A | 5/1998 | Medford et al. | |
| 5,773,209 A | 6/1998 | Medford et al. | |
| 5,773,231 A | 6/1998 | Medford et al. | |
| 5,807,884 A | 9/1998 | Medford et al. | |
| 5,811,449 A | 9/1998 | Medford et al. | |
| 5,846,959 A | 12/1998 | Medford et al. | |
| 6,121,319 A | 9/2000 | Somers et al. | |
| 6,147,250 A | 11/2000 | Somers | |
| 6,548,699 B1* | 4/2003 | Somers ............ | 562/431 |
| 6,602,914 B2 | 8/2003 | Meng | |
| 6,617,352 B2 | 9/2003 | Somers | |
| 6,828,447 B2 | 12/2004 | Meng | |
| 6,852,878 B2* | 2/2005 | Meng et al. ............ | 562/42 |
| 6,881,860 B2 | 4/2005 | Sikorski et al. | |
| 2002/0193446 A1 | 12/2002 | Meng | |
| 2003/0064967 A1 | 4/2003 | Luchoomun et al. | |
| 2004/0266879 A1 | 12/2004 | Sikorski et al. | |
| 2005/0065121 A1 | 3/2005 | Sikorski et al. | |
| 2005/0090487 A1 | 4/2005 | Somers | |
| 2005/0171028 A1 | 8/2005 | Meng et al. | |

FOREIGN PATENT DOCUMENTS

| | | |
|---|---|---|
| EP | 0 348 203 A1 | 12/1989 |
| EP | 0 405 788 A2 | 1/1991 |
| EP | 0 621 255 A1 | 10/1994 |

(Continued)

OTHER PUBLICATIONS

Barnhart, J.W., et al., "Chapter 10: The Synthesis, metabolism, and biological activity of probucol and its analogs," *Pharmacochem. Libr.*, in Antilipidemic Drugs: Medicinal, Chemical, and Biochemical Aspects, Witiak et al., Eds., (Elsevier Science: Amsterdam, 1991), pp. 277-299.

Baron, J.L., et al., "The pathogenesis of adoptive murine autoimmune diabetes requires an interaction between a4-integrins and vascular cell adhesion molecule-1," *J. Clin. Invest.*, 93(4-6):1700-1708 (1994).

(Continued)

*Primary Examiner*—Shailendra Kumar
(74) *Attorney, Agent, or Firm*—King & Spalding

(57) ABSTRACT

The invention relates to compounds, pharmaceutical compositions comprising the compounds, and methods of using the compounds, wherein the compounds are of the following Formulas:

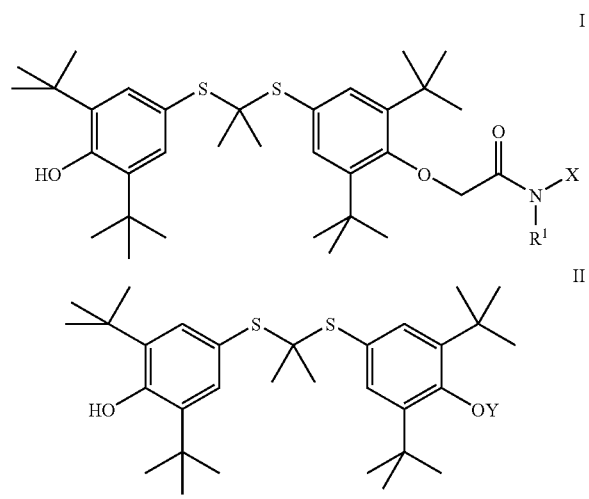

or a pharmaceutically acceptable salt, ester or prodrug thereof, wherein the substituents are defined in the application. The invention further provides methods of treatment of inflammatory disorders by administering the compounds.

25 Claims, No Drawings

FOREIGN PATENT DOCUMENTS

| | | |
|---|---|---|
| EP | 0 763 527 A1 | 3/1997 |
| FR | 2130975 A5 | 11/1972 |
| FR | 2133024 A5 | 11/1972 |
| FR | 2134810 A5 | 12/1972 |
| FR | 2140769 A5 | 1/1973 |
| FR | 2140771 A5 | 1/1973 |
| FR | 2168137 A1 | 8/1973 |
| WO | WO95/15760 A1 | 6/1995 |
| WO | WO95/30415 A1 | 11/1995 |
| WO | WO97/15546 A1 | 5/1997 |
| WO | WO98/51289 A2 | 11/1998 |
| WO | WO98/51662 A1 | 11/1998 |
| WO | WO 00/26184 A1 | 5/2000 |
| WO | WO 01/07057 A2 | 9/2001 |

OTHER PUBLICATIONS

Burkly, L.C., et al., "Protection against adoptive transfer of autoimmune diabetes mediated through very late antigen-4 integrin," *Diabetes*, 43:529-534 (1994).

Carew, T.E., et al., "Antiatherogenic effect of probucol unrelated to its hypocholesterolemic effect: Evidene that antioxidants *in vivo* can selectively inhibit low density lipoprotein degradation in macrophage-rich fatty streaks and slow the progression of atherosclerosis in the Watanabe heritable hyperlipidemic rabbit," *Proc. Natl. Acad. Sci. U.S.A.*, 84:7725-7729 (Nov. 1987).

De Meglio, P., et al. "New derivatives of clofibrate and probucol. Preliminary studies on hypolipe-mic activity," *Farmaco, Ed. Sci.*, 40(11), 833-844 (1985). [In Italian; abstract provided in English: *Chem Abstr.* AN 1986:28675, DN 104:28675; & partial translation in English.

Elovaara, I., et al., "Adhesion Moleules in Multiple Sclerosis," *Arch. Neurol.*, 57:546-551 (2000).

Folkman, J. and Shing, Y., "Angiogenesis," *J. Biol. Chem.*, 267(16):10931-10934 (Jun. 5, 1992).

Foster, C.A., et al., "Novel Inhibitor of Endothelial Cell-Associated VCAM-1 Expression," *Skin Pharmacol.*, 9:149 (from 12th Annual Meeting at pp. 141-168) (1996).

Haddad, J.J., et al., "Redox regulation of TNF-alpha biosynthesis: augmentation by irreversible inhibition of gamma-glutamylcysteine synthetase and the involvement of an IkappaB-alpha/NF-kappa.B-independent pathway in alveolar epithelial cells," *Cell Signal*, 14(3):211-218 (Mar. 2002).

Kallmann, B.A., et al., "Cytokine-induced modulation of cellular adhesion to human cerebral endothelial cells is mediated by soluble vascular cell adhesion molecule-1," *Brain*, 123:687-697 (2000).

Koch, A.E., et al., "Immunolocalization of endothelial and leukocyte adhesion molecules in human rheumatoid and osteoarthritic synovial tissues", *Lab. Investig.*, 64(3):313-320 (1991).

Koch, A.E., et al., "Angiogenesis mediated by soluble forms of E-selectin and vascular cell adhesion molecule-1," *Nature*, 376(6540):517-519 (Aug. 10, 1995).

Kudlacz, E., et al., "Pulmonary eosinophilia in a murine model of allergic inflammation is attenuated by small molecule alpha4beta1 antagonists," *J. Pharmacol. Exp. Ther.*, 301(2):747-752 (May 2002).

Lee, S.J., et al., "Adhesion molecule expression and regulation on cells of the central nervous system," *J. Neuroimmunol.*, 98:77-88 (1998).

Marx, N., et al., "Peroxisome proliferator-activated receptors (PPARs) and their role in the vessel wall: possible mediators of cardiovascular risk?" *J. Cardiovasc. Risk*, 8(4):203-210 (Aug. 2001).

Meng, C.Q., et al., "Nitrobenzene compounds inhibit expression of VCAM-1," *Bioorganic & Medicinal Chemistry Letters*, 11(14):1823-1827 (Jul. 23, 2001).

Meng, C.Q., et al., "Novel phenolic antioxidants as multifunctional inhibitors of inducible VCAM-1 expression for use in atherosclerosis," *Bioorganic & Medicinal Chemistry Letters*, 12:2545-2548 (2002).

Meng, C.Q., "Probucol (Restenosis) Daiichi," *Curr. Opin. Cardiovasc. Pulm. Renal Invest. Drugs*, 2(3):294-298 (2000).

Morales-Ducret, J., et al., "$\alpha 4/\beta 1$ integrin (VLA-4) ligands in arthritis: vascular cell adhesion molecule-1 expression in synovium and on fibroblast-like synoviocytes", *J. Immunol.*, 149(4):1424-1431 (Aug. 15, 1992).

Nakao, H., et al., "An Inhibitor of VCAM-1 Expression and Its Implication as a Novel Treatment of Inflammatory Disease," *J. Atheroscler. Thromb.*, 4:149-155 (1998).

Nicolaou, K.C., et al., "Total Synthesis of Ionophore Antibiotic X-14547A," *J. Org. Chem.*, 50:1440-1456 (1985).

Oguchi, S., et al., "Monoclonal Antibody Against Vascular Cell Adhesion Molecule-1 Inhibits Neointimal Formation after Periadventitial Carotid Artery Injury in Genetically Hypercholesterolemic Mice," *Arterioscler. Thromb. Vasc. Biol.*, 20:1729-1736 (2000).

Ohkawara, Y., et al., "*In situ* expression of the cell adhesion molecules in bronchial tissues form asthmatics with air flow limitation: *In vivo* evidence of VCAM-1/VLA-4 interaction in selective eosinophil infiltration," *Am. J. Respir. Cell Mol. Biol.*, 12:4-12 (1995).

Pilewski, J.M., et al., "Cell Adhesion Molecules is Asthma: Homing, Activation, and Airway Remodeling," *Am. J. Respir. Cell. Mol. Biol.*, 12:1-3 (1995).

Rabb, H.A., et al., "The Role of the Leukocyte Adhesion Molecules VLA-4, LFA-1, and Mac-1 in Allergic Airway Responses in the Rat," *Am. J. Respir. Care. Med.*, 149:1186-1191 (1994).

Rival, Y., et al., "PPARalpha and PPARdelta activators inhibit cytokine-induced nuclear translocation of NF-kappaB and expression of VCAM-1 in EAhy926 endothelial cells," *Eur. J. Pharmacol.*, 435(2-3)143-151 (Jan. 25, 2002).

Schreiner, E.P., et al., "Inhibitors of vascular cell adhesion molecule-1 expression," *Expert Opin. Ther. Patents*, 13(2):149-166 (2003).

Tardif, J.C., et al., "Effects of AGI-1067 and probucol after percutaneous coronary interventions," *Circulation*, 107(4):552-558 (Feb. 4, 2003).

Yang, X.D., et al., "Inhibition of insulitis and prevention of diabetes in nonobese diabetic mice by blocking L-selectin and very late antigen 4 adhesion receptors," *Proc. Natl. Acad. Sci. U.S.A.*, 90(22):10494-10498 (Nov. 15, 1993).

\* cited by examiner

US 7,271,274 B2

PHENOLIC ANTIOXIDANTS FOR THE TREATMENT OF DISORDERS INCLUDING ARTHRITIS, ASTHMA AND CORONARY ARTERY DISEASE

CROSS REFERENCE TO RELATED APPLICATIONS

This application claims priority to U.S. Provisional Patent Application Ser. Nos. 60/564,043 filed Apr. 20, 2004 and 60/600,029 filed Aug. 9, 2004.

FIELD OF THE INVENTION

This invention is phenolic antioxidants that can be used for the treatment of disorders in which redox-sensitive pro-inflammatory genes are involved including VCAM-1, such as arthritis, asthma and coronary artery disease.

BACKGROUND OF THE INVENTION

VCAM-1 is also a mediator of chronic inflammatory disorders such as asthma, rheumatoid arthritis, autoimmune diabetes and multiple sclerosis. For example, it is known that the expression of VCAM-1 and ICAM-1 are increased in asthmatics (Pilewski, J. M., et al. *Am. J. Respir. Cell Mol. Biol.* 12, 1–3 (1995); Ohkawara, Y., et al., *Am. J. Respir. Cell Mol. Biol.* 12, 4–12 (1995)). Additionally, blocking the integrin receptors for VCAM-1 and ICAM-1 (VLA-4 and LFA-1, respectively) suppressed both early and late phase responses in an ovalbumin-sensitized rat model of allergic airway responses (Rabb, H. A., et al., *Am. J. Respir. Care Med.* 149, 1186–1191 (1994)). There is also increased expression of endothelial adhesion molecules, including VCAM-1, in the microvasculature of rheumatoid synovium (Koch, A. E. et al., *Lab. Invest.* 64, 313–322 (1991); Morales-Ducret, J. et al., *Immunol.* 149, 1421–1431 (1992)). Neutralizing antibodies directed against VCAM-1 or its counter receptor, VLA-4, can delay the onset of diabetes in a mouse model (NOD mice) which spontaneously develops the disease (Yang, X. D. et al., *Proc. Natl. Acad. Sci. U.S.A.* 90, 10494–10498 (1993); Burkly, L. C. et al., *Diabetes* 43, 523–534 (1994); Baron, J. L. et al., *J. Clin. Invest.* 93, 1700–1708 (1994)).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea (Koch, A. F. et al., *Nature* 376, 517–519 (1995)). Inhibitors of the expression of soluble VCAM-1 have potential therapeutic value in treating diseases with a strong angiogenic component, including tumor growth and metastasis (Folkman, J. and Shing, Y., *Biol. Chem.* 10931–10934 (1992)).

VCAM-1 is expressed in cultured human vascular endothelial cells after activation by lipopolysaccharide (LPS) and cytokines such as interleukin-1 (IL-1) and tumor necrosis factor (TNF-alpha).

It has been documented that VCAM-1 is expressed on brain microvessel endothelial cells in active lesions of multiple sclerosis brain. Multiple sclerosis is a common demyelinating disorder of the central nervous system, causing patches of sclerosis (plaques) in the brain and spinal cord. It occurs in young adults and has protean clinical manifestations. Experimental therapy using antibodies for VCAM-1 in autoimmune encephalomyelitis, which is an animal model for multiple sclerosis, has shown that adhesion molecules play a role in the pathogenesis of the disease (Benveniste et al., *J. Neuroimmunol.* 98:77–88, 1999). Time and dose dependent expression of VCAM-1 and release of soluble VCAM-1 were detected in cultures of human cerebral endothelial cells induced by TNF-alpha, but not in peripheral blood mononuclear cells (Kallmann et al., *Brain* 123:687–697, 2000). Clinical data also show that adhesion molecules in blood and cerebrospinal fluid are up-regulated throughout the clinical spectrum of multiple sclerosis, further supporting the belief that multiple sclerosis can be suppressed by interfering with cell adhesion molecules such as VCAM-1 (Elovaara et al., *Arch. Neurol.* 57:546–551, 2000).

A variety of agents have been reported as potent inhibitors of VCAM-1 expression. (Schreiner et al., *Expert Opi. Ther. Patents* 2003, 13, 149–166; Meng et al., *Bioorg. Med. Chem. Lett.* 2001, 11, 1823–1827.) A cyclic depsipeptide effectively inhibited VCAM-1 expression and reduced inflammation in a dermal model of inflammation (Foster et al., *Skin Pharmacol.* 1996, 9, 149). A monoclonal antibody against VCAM-1 inhibited neointimal formation in a murine model of arterial wall injury. (Oguchi et al., *Arterioscler. Thromb. Vasc. Biol.* 2000, 20, 1729–1736.) A disubstituted 1,4-diazepine diminished the increase in paw swelling in a mouse model of collagen-induced arthritis. (Nakao et al., *J. Atheroscler. Thromb.* 1998, 4, 149–155.) Some VLA-4 antagonists have shown efficacy in animal models of disease. CP-664511, a small-molecule VLA-4 antagonist in clinical trials in asthmatic patients, inhibited airway eosinophil infiltration in a murine model of allergic pulmonary inflammation. (Kudlacz et al., *J. Pharmacol. Exp. Ther.* 2002, 301, 747–752.) Several activators of peroxisome proliferator-activated receptors (PPARs) inhibited the expression of VCAM-1 on endothelial cells, suggesting a role of VCAM-1 in the anti-inflammatory response of PPAR activation. (Marx et al., *J. Cardiovasc. Risk* 2001, 8, 203–210; and Rival et al., *Eur. J. Pharmacol.* 2002, 435, 143–151.)

Probucol has been shown to possess potent antioxidant properties and to block oxidative modification of LDL. Consistent with these findings, probucol has been shown to actually slow the progression of atherosclerosis in LDL receptor-deficient rabbits. (Carew et al. *Proc. Natl. Acad. Sci. U.S.A.* 84:7725–7729 (1987); Meng, C. Q. Probucol (Restenosis). *Curr. Opin. Cardiovasc. Pulm. Renal Invest. Drugs* 2000, 2, 294–298; Barnhart et al., The Synthesis, Metabolism, and Biological Activity of Probucol and Its Analogs. In *Antilipidemic Drugs: Medicinal, Chemical, and Biochemical Aspects*, Witiak et al., Eds., Elsevier Science: Amsterdam, 1991, pp 277–299.)

Probucol is chemically related to the widely used food additives 2,(3)-tert-butyl-4-hydroxyanisole (BHA) and 2,6-di-tert-butyl-4-methyl phenol (BHT). It is a thioketal having a chemical name of 4,4'-(isopropylidenedithio) bis(2,6-di-tert-butylphenol) and has the following chemical structure:

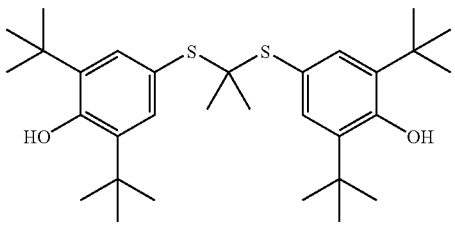

While probucol is a potent chemical anti-oxitant, there is little data to indicate it can be used in inflammatory diseases that do not depend on changing lipid levels such as sheumatoid arthritis, asthma and COPD. It is used primarily to lower serum cholesterol levels in hypercholesterolemic patients. Probucol is commonly administered in the form of tablets available under the trademark Lorelco™.

U.S. Pat. No. 5,262,439 to Parthasarathy discloses analogs of probucol with increased water solubility in which one or both of the hydroxyl groups are replaced with ester groups.

Certain probucol ester derivatives have been described as being hypocholesterolemic and hypolipidemic agents: Fr 2168137 (bis 4-hydroxyphenylthioalkane esters); Fr 2140771 (tetralinyl phenoxy alkanoic esters of probucol); Fr 2140769 (benzofuryloxyalkanoic acid derivatives of probucol); Fr 2134810 (bis-(3-alkyl-5-t-alkyl-4-thiazole-5-carboxy)phenyl-thio)alkanes; FR 2133024 (bis-(4-nicotinoyloxyphenylthio)propanes; and Fr 2130975 (bis(4-(phenoxyalkanoyloxy)-phenylthio)alkanes).

De Meglio et al. have described several ethers of symmetrical molecules for the treatment of hyperlipidemia. These molecules contain two phenyl rings attached to each other through a —S—C(CH$_3$)$_2$—S— bridge. In contrast to probucol, the phenyl groups do not have t-butyl as substituents. (De Meglio et al., *New Derivatives of Clofibrate and probucol: Preliminary Studies of Hypolipemic Activity*; Farmaco, Ed. Sci (1985), 40 (11), 833–44).

WO 00/26184 discloses a large genus of compounds with a general formula of phenyl-S-alkylene-S-phenyl, in which one or both phenyl rings can be substituted at any position. These compounds were disclosed as lubricants.

U.S. Pat. Nos. 5,750,351; 5,807,884; 5,811,449; 5,846,959; 5,773,231, and 5,773,209 to Medford, et al. (assigned to Emory University), as well as the corresponding WO95/30415 to Emory University indicate that polyunsaturated fatty acids ("PUFAs") and their hydroperoxides ("ox-PUFAs"), which are important components of oxidatively modified low density lipoprotein (LDL), induce the expression of VCAM-1, but not intercellular adhesion molecule-1 (ICAM-1) or E-selectin in human aortic endothelial cells.

U.S. Pat. No. 5,155,250 to Parker et al. discloses that 2,6-dialkyl-4-silylphenols are antiatherosclerotic agents. The same compounds are disclosed as serum cholesterol lowering agents in PCT Publication No. WO 95/15760, published on Jun. 15, 1995. U.S. Pat. No. 5,608,095 to Parker et al. discloses that alkylated-4-silyl-phenols inhibit the peroxidation of LDL, lower plasma cholesterol, and inhibit the expression of VCAM-1, and thus are useful in the treatment of atherosclerosis.

A series of European patent applications of Shionogi Seiyaku Kabushiki Kaisha disclose phenolic thioethers for use in treating arteriosclerosis. European Patent Application No. 348 203 discloses phenolic thioethers which inhibit the denaturation of LDL and the incorporation of LDL by macrophages. The compounds are useful as anti-arteriosclerosis agents. Hydroxamic acid derivatives of these compounds are disclosed in European Patent Application No. 405 788 and are useful for the treatment of arteriosclerosis, ulcer, inflammation and allergy. Carbamoyl and cyano derivatives of the phenolic thioethers are disclosed in U.S. Pat. No. 4,954,514 to Kita et al.

U.S. Pat. No. 4,752,616 to Hall et al. discloses arylthioalkylphenylcarboxylic acids for the treatment of thrombotic disease. The compounds disclosed are useful as platelet aggregation inhibitors for the treatment of coronary or cerebral thromboses and the inhibition of bronchoconstriction, among others.

A series of patents to Adir et Compagnie disclose substituted phenoxyisobutyric acids and esters useful as antioxidants and hypolipaemic agents. This series includes U.S. Pat. Nos. 5,206,247 and 5,627,205 to Regnier, et al. (which corresponds to European Patent Application No. 621 255) and European Patent Application No. 763 527.

WO 97/15546 to Nippon Shinyaku Co. Ltd. discloses carboxylic acid derivatives for the treatment of arterial sclerosis, ischemic heart diseases, cerebral infarction and post PTCA restenosis.

The Dow Chemical Company is the assignee of patents to hypolipidemic 2-(3,5-di-tert-butyl-4-hydroxyphenyl)thio carboxamides. For example, U.S. Pat. Nos. 4,029,812, 4,076,841 and 4,078,084 to Wagner, et al., disclose these compounds for reducing blood serum lipids, especially cholesterol and triglyceride levels.

PCT WO 98/51289, filed by Emory University and listing as inventors Russell M. Medford and Patricia K. Somers, claims priority to provisional patent application U.S. Ser. No. 60/047,020, filed on May 14, 1997. This application discloses that monoesters of probucol inhibit the expression of VCAM-1, and may also exhibit the composite profile of lowering LDL and reducing cholesterol.

Recent reports demonstrated that mono-esters potently inhibited cytokine-induced VCAM-1 and MCP-1 expression and smooth muscle cell proliferation in vitro, and progression of atherosclerosis in experimental animals. (Meng et al., *Bioorg. Med. Chem. Lett.* 2002, 12, 2545–2548. In clinical trials, AGI-1067 did not cause QTc prolongation, while probucol did. Tardif et al., *Circulation* 2003, 107, 552–558.)

PCT WO 98/51662 and U.S. Pat. Nos. 6,147,250, 6,548, 699, 6,617,352 and 6,602,914 describe mono-esters of probucol for the treatment of VCAM-1 mediated diseases including cardiovascular and inflammatory diseases. PCT US 01/09049 discloses thioketals and thioethers for the treatment of VCAM-1 mediated diseases including inflammatory disorders.

There is a need for new phenolic compounds that can be used in the treatment of a variety of disorders.

SUMMARY OF THE INVENTION

In one embodiment, antioxidant compounds are provided that inhibit the expression of redox-sensitive pro-inflammatory genes, including VCAM-1, and can be used to treat a patient with a disorder in which VCAM-1 expression is involved. Since VCAM-1 can be a mediator or marker of chronic inflammatory disorders, the compounds, compositions and methods of the invention can be used to inhibit the expression of VCAM-1 and to treat chronic inflammatory disorders including cardiovascular and inflammatory diseases.

Compounds of the present invention include those of Formula I

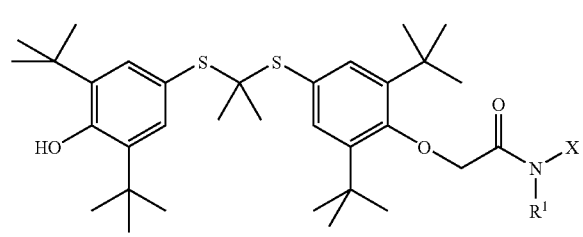

or a pharmaceutically acceptable salt or ester thereof, wherein

R$^1$ is independently hydrogen or optionally substituted C$_1$–C$_4$ alkyl; and X is independently C$_1$–C$_4$ alkyl, optionally substituted by one or more hydroxyl or C(O)OH wherein the one or more hydroxyl or C(O)OH groups are optionally protected with a protecting group.

In another embodiment, a compound of Formula II is provided:

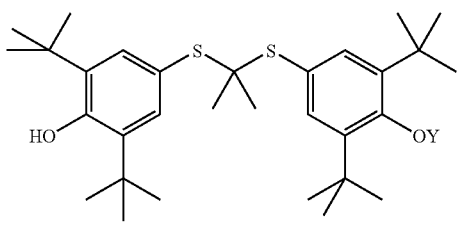

II wherein Y is selected from the group consisting of:

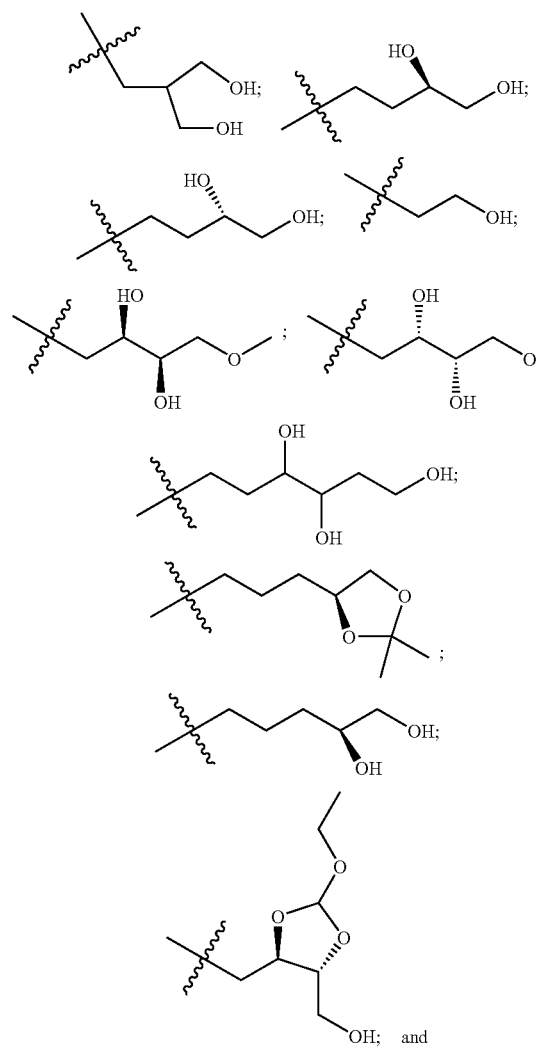

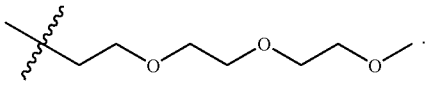

In yet another embodiment of the invention, a compound is provided of Formula II above wherein Y is selected from the group consisting of:

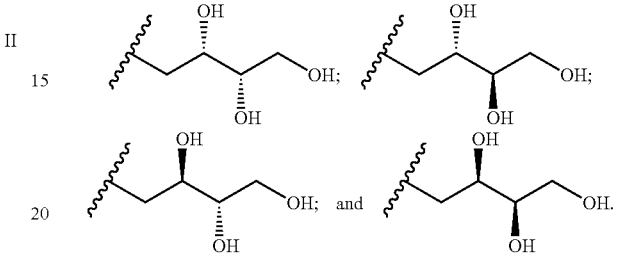

Examples of inflammatory disorders in which VCAM-1 expression is involved and that can be treated or prophylactically treated, as disclosed herein include, but are not limited to arthritis, rheumatoid arthritis, asthma, dermatitis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, allergic rhinitis, ocular inflammation, uveitis, ischemia-reperfusion injury, stenosis, restenosis, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

In a particular embodiment, compounds, compositions and methods are provided for the treatment rheumatoid arthritis. The compounds and compositions of the invention are also suitable as disease modifying anti-rheumatoid arthritis drugs (DMARDs). The compounds, methods and compositions disclosed herein also can be used for the treatment of ocular inflammation, including uveitis.

In a particular embodiment, compounds, compositions and methods are provided for the treatment asthma, or other pulmonary inflammatory diseases. The compounds and compositions of the invention are also suitable as disease modifying anti-asthma drugs. In another embodiment, the compounds and compositions of the invention can be used to treat chronic obstructive pulmonary disease.

In another embodiment, the compounds described herein are useful in both the primary and adjunctive medical treatment of cardiovascular disease. The compounds can be used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy. Compounds, methods and compositions of the invention can be used to inhibit the progression of atherosclerosis.

The compounds, compositions and methods disclosed herein can also be used in the treatment of inflammatory skin diseases as well as human endothelial disorders, which include, but are not limited to psoriasis, dermatitis, including eczematous dermatitis, Kaposi's sarcoma, multiple sclerosis, as well as proliferative disorders of smooth muscle cells.

In yet another embodiment, the compounds, methods and compositions disclosed herein can be selected to treat anti-inflammatory conditions that are mediated by mononuclear leucocytes. Further, they can be used to treat inflammatory diseases by modulating the expression of pro-inflammatory genes such as TNFα, IL1β, MCP-1 and IL6.

In one embodiment, the compounds, methods and compositions disclosed herein are used in the prevention or treatment of tissue or organ transplant rejection. Treatment and prevention of organ or tissue transplant rejection includes, but is not limited to the treatment of recipients of heart, lung, combined heart-lung, liver, kidney, pancreatic, skin, spleen, small bowel, or corneal transplants. The compounds, methods and compositions disclosed herein can also be used in the prevention or treatment of graft-versus-host disease, such as sometimes occurs following bone marrow transplantation.

The compounds, methods and compositions can be used alone or as adjunct or combination therapy simultaneously or in series.

Also provided are pharmaceutical compositions comprising a compound disclosed herein in a form suitable for oral, parenteral, intravenous, intradermal, transdermal, subcutaneous or topical administration. The pharmaceutical composition is, e.g., in the form of a tablet or capsule. The compounds may be substantially free of other stereoisomer forms, and essentially enantiamerically pure.

Also within the scope of the invention is the use of a compound disclosed herein, or a pharmaceutically acceptable salt or ester thereof, or the use in the manufacture of a medicament, optionally with a pharmaceutically acceptable carrier or diluent, for the treatment of an inflammatory disease in a host, optionally in combination and/or alternation with one or more other therapeutic agents such as anti-inflammatory agents.

DETAILED DESCRIPTION OF THE INVENTION

I. Definitions

The term "alkyl", as used herein, unless otherwise specified, includes a saturated straight, branched, or cyclic, primary, secondary, or tertiary hydrocarbon of typically $C_1$ to $C_4$, and specifically includes methyl, ethyl, propyl, isopropyl, cyclopropyl, butyl, isobutyl, secbutyl, and t-butyl. The alkyl is optionally substituted. Substituted alkyl groups include halogenated alkyl groups, including fluorinated alkyl. groups. The alkyl group may be optionally substituted with a moiety such as halo (chloro, fluoro, bromo or iodo), haloalkyl, hydroxyl, carboxyl, acyl, aryl, acyloxy, amino, amido, carboxyl derivatives, alkylamino, dialkylamino, arylamino, alkoxy, aryloxy, nitro, cyano, carboxylic acid, and carbamate, either unprotected, or protected as necessary, as known to those skilled in the art, for example, as taught in Greene et al., *Protective Groups in Organic Synthesis*, John Wiley & Sons, Second Edition, 1991. Examples include $CF_3$ and $CH_2CF_3$.

Whenever a range of is referred to herein, it includes independently and separately every member of the range. As a nonlimiting example, the term "$C_1$–$C_4$ alkyl" (or $C_{1-4}$ alkyl) is considered to include, independently, each member of the group, such that, for example, $C_1$–$C_4$ alkyl includes straight, branched and where appropriate cyclic $C_1$, $C_2$, $C_3$ and $C_4$ alkyl functionalities.

As used herein, the term "compound substantially free of" or "compound substantially in the absence of" refers to a form of a compound that is in an admixture with no more than 15%, or no more than 10% by weight, or no more than 5%, 2%, 1% or 0% by weight, of other enantiomeric or diastereomeric or other stereoisomeric forms of that compound.

In one embodiment, in the methods, compositions and compounds of this invention, when stereochemistry is designated, the compounds are substantially free of their enantiomers or other stereoisomeric forms.

Similarly, the term "isolated" refers to a compound that includes at least 85%, 90%, 95%, 98%, 99%, or 100% by weight, of the compound, the remainder comprising other compounds.

The term "pharmaceutically acceptable salt" refer to a salt or complex that retains the desired biological activity of a compound of the present invention and exhibits minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from meglumine, ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt comprising a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). Other examples of pharmaceutically acceptable salts are organic acid addition salts formed with acids which form a physiological acceptable anion, for example, arginine, lysine, tosylate, methanesulfonate, citrate, α-ketoglutarate, and α-glycerophosphate. Suitable inorganic salts may also be formed, including, sulfate, nitrate, bicarbonate, and carbonate salts.

As used herein, the term "prodrug" includes a compound that, when administered to a subject, is converted under physiological conditions to a compound of the invention.

As used herein, the term "patient" refers to a warm-blooded animal or mammal, and in particular a human, in need of therapy. The term "host", as used herein, refers to a unicellular or multicellular organism, including cell lines and animals, including a human.

II. Description

It has been discovered that the phenolic antioxidant compounds of the invention inhibit the expression of VCAM-1, and thus can be used to treat a patient with a disorder in which VCAM-1 expression is involved and/or certain redox-sensitive pro-inflammatory genes are involved such as TNFα, IL1β, MCP-1 and IL6. These compounds can be administered to a host as monotherapy, or if desired, in combination with another compound of the invention or another biologically active agent, as described in more detail below.

A. Compounds

In one embodiment, there is provided a compound of Formula I:

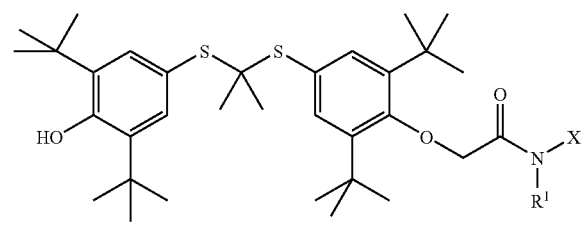

I wherein $R^1$ is independently hydrogen or $C_1$–$C_4$ alkyl; and

X is independently $C_1$–$C_4$ alkyl, optionally substituted by one or more hydroxyl or C(O)OH, which are optionally protected.

In one embodiment, the one or more hydroxyl or C(O)OH groups are protected.

Optionally, X is $C_1$–$C_4$ alkyl substituted by two or more hydroxyl groups.

Optionally, X is $C_1$–$C_4$ alkyl substituted by three or more hydroxyl groups.

Optionally, $R^1$ is substituted $C_1$–$C_4$ alkyl, e.g., substituted with a halogen, such as fluoro.

X is, e.g., a $C_1$, $C_2$, $C_3$ or $C_4$ alkyl.

Specific embodiments include:

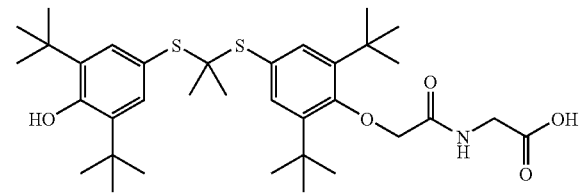

(2-{2,6-Di-tert-butyl-4-[1-(3,5-di-tert-butyl-4-hydroxyphenylsulfanyl)-1-methylethylsulfanyl]phenoxy}acetylamino)acetic acid;

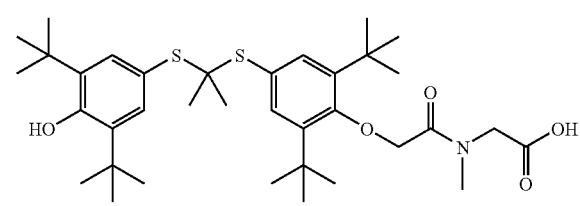

[(2-{2,6-Di-tert-butyl-4-[1-(3,5-di-tert-butyl-4-hydroxyphenylsulfanyl)-1-methylethylsulfanyl]phenoxy}acetyl)methylamino]acetic acid;

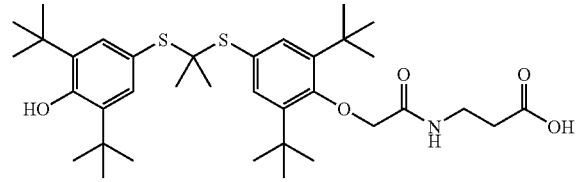

3-(2-{2,6-Di-tert-butyl-4-[1-(3,5-di-tert-butyl-4-hydroxyphenylsulfanyl)-1-methylethylsulfanyl]phenoxy}acetylamino)propionic acid; and

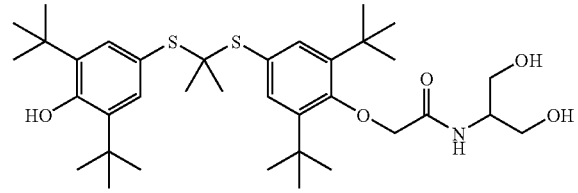

2-{2,6-Di-tert-butyl-4-[1-(3,5-di-tert-butyl-4-hydroxyphenylsulfanyl)-1-methyl-ethylsulfanyl]phenoxy}-N-(2-hydroxy-1-hydroxymethyl-ethyl)acetamide.

In one embodiment, there is provided a compound of Formula II:

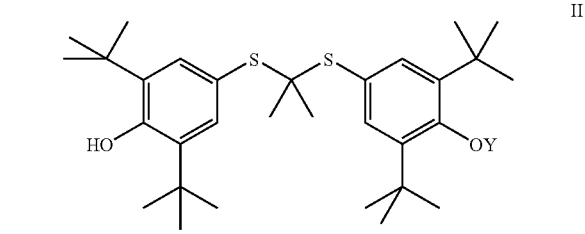

II wherein Y is selected from the group consisting of:

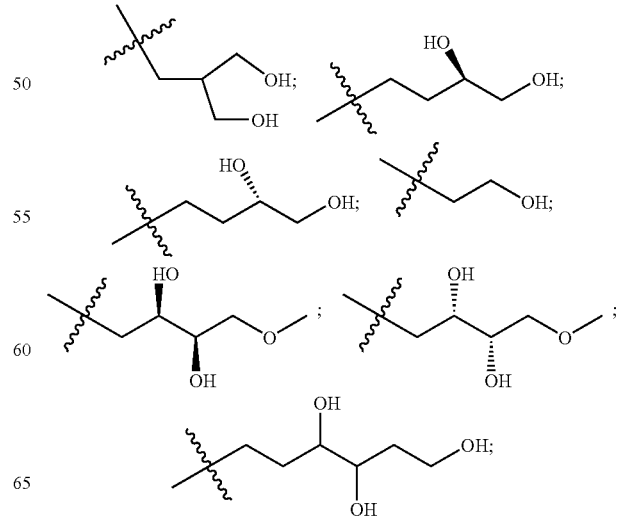

-continued

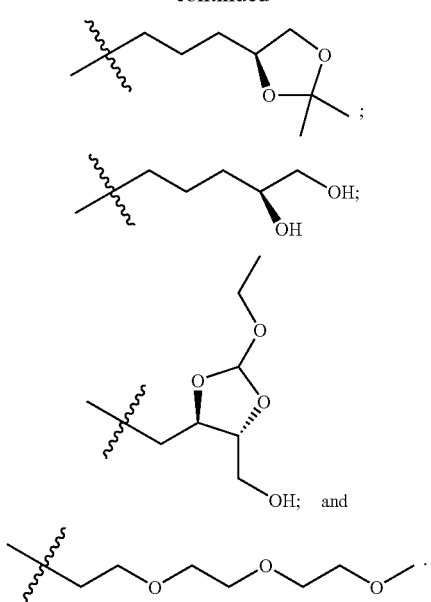

The compounds specifically include the following:

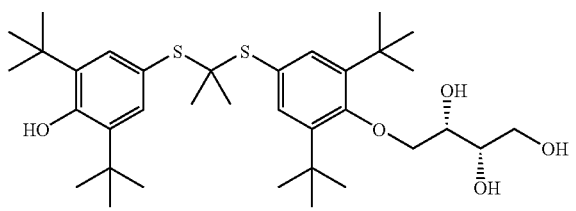

4-{2,6-Di-tert-butyl-4-[1-(3,5-di-tert-butyl-4-hydroxyphenylsulfanyl)-1-methylethylsulfanyl]phenoxy}butane-1,2(S),3(S)-triol;

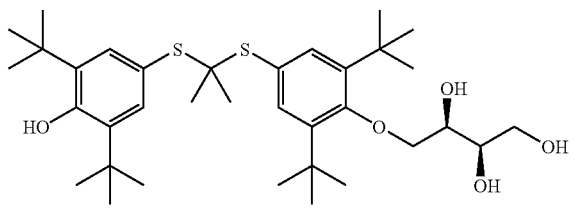

4-{2,6-Di-tert-butyl-4-[1-(3,5-di-tert-butyl-4-hydroxyphenylsulfanyl)-1-methylethylsulfanyl]-phenoxy}butane-1,2(R),3(R)-triol;

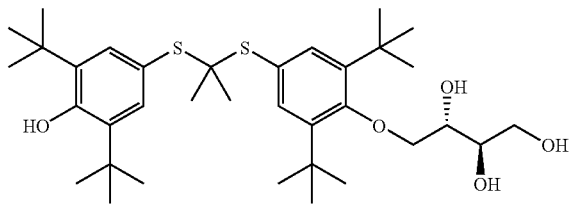

4-{2,6-Di-tert-butyl-4-[1-(3,5-di-tert-butyl-4-hydroxyphenylsulfanyl)-1-methylethylsulfanyl]-phenoxy}butane-1,2(S),3(R)-triol; and

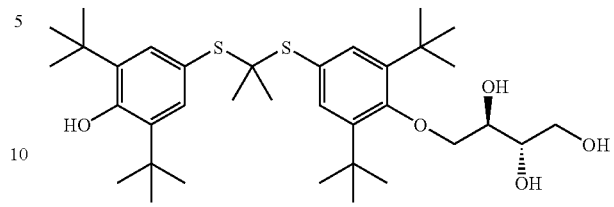

4-{2,6-Di-tert-butyl-4-[1-(3,5-di-tert-butyl-4-hydroxyphenylsulfanyl)-1-methylethylsulfanyl]-phenoxy}butane-1,2(R),3(S)-triol.

In yet another embodiment of the invention, a compound is provided of Formula II above wherein Y is selected from the group consisting of:

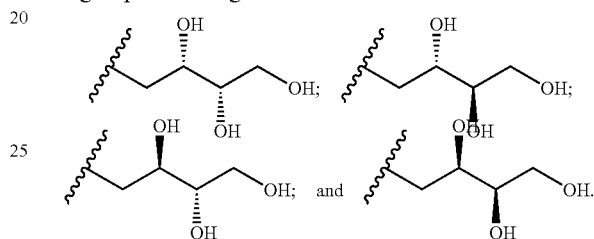

A further embodiment includes the intermediates used to make the final compounds of the invention. Said intermediates are useful as starting materials for making the compounds of the invention as well as having pharmaceutical activity alone.

Another embodiment of the invention includes the process for making both the intermediates as well as the final compounds.

B. Synthesis of Active Compounds

The compounds of the present invention can be prepared by those skilled in the art of organic synthesis using the methods disclosed herein and techniques known in the art, many of which are described by J. March, in *Advanced Organic Chemistry*, 4$^{th}$ Edition (Wiley-Interscience, New York, 1992), incorporated herein by reference.

Specific means of preparing the compounds of the invention are schematically displayed below.

SCHEME 1

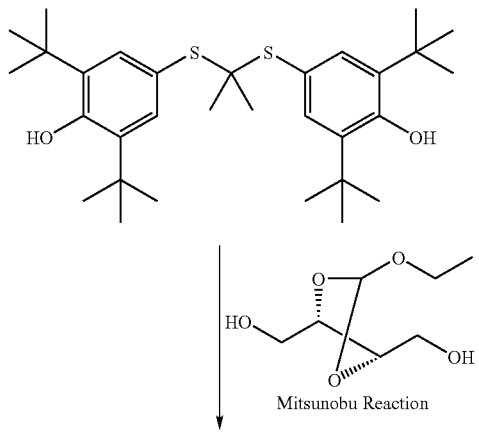

Mitsunobu Reaction

-continued
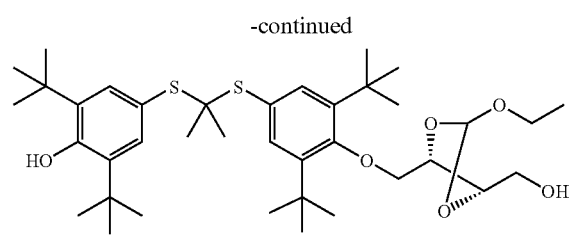
↓ R—X, Base
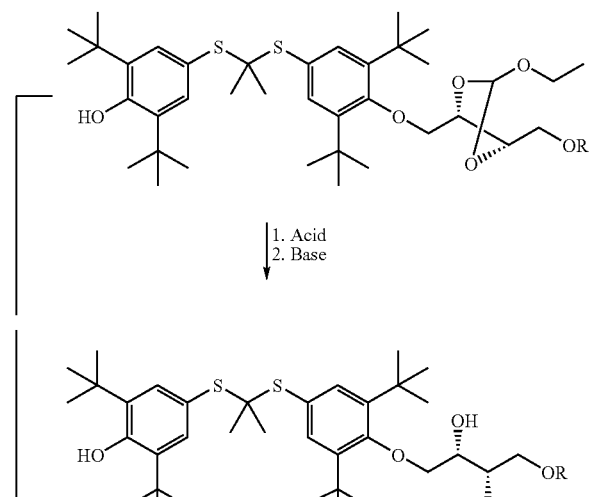
1. Acid
2. Base
↓
1. Acid
2. Base
↓
R is alkyl and X is halide
SCHEME 2
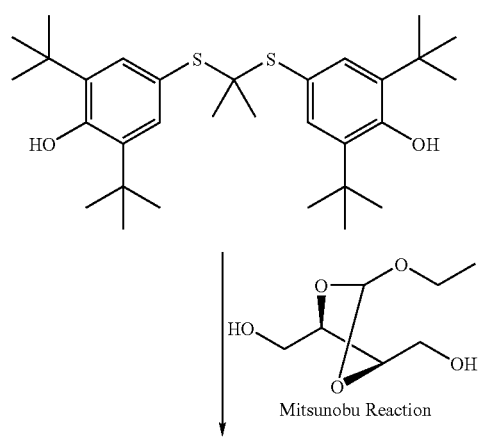
Mitsunobu Reaction
↓
-continued
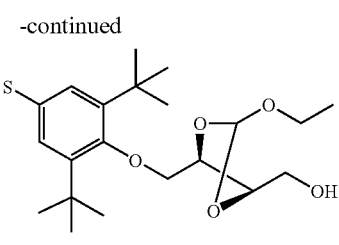
↓ R—X, Base
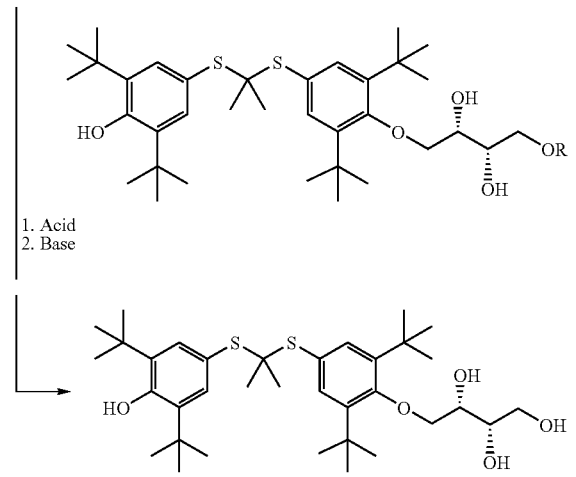
1. Acid
2. Base
↓
1. Acid
2. Base
↓
R is alkyl and X is halide
SCHEME 3
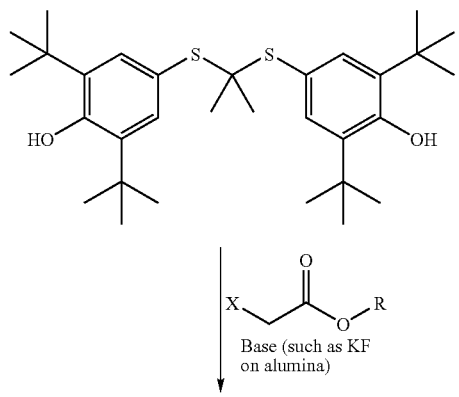
Base (such as KF on alumina)
↓

-continued

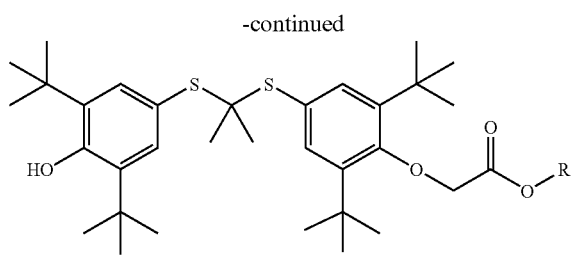

Base hydrolysis

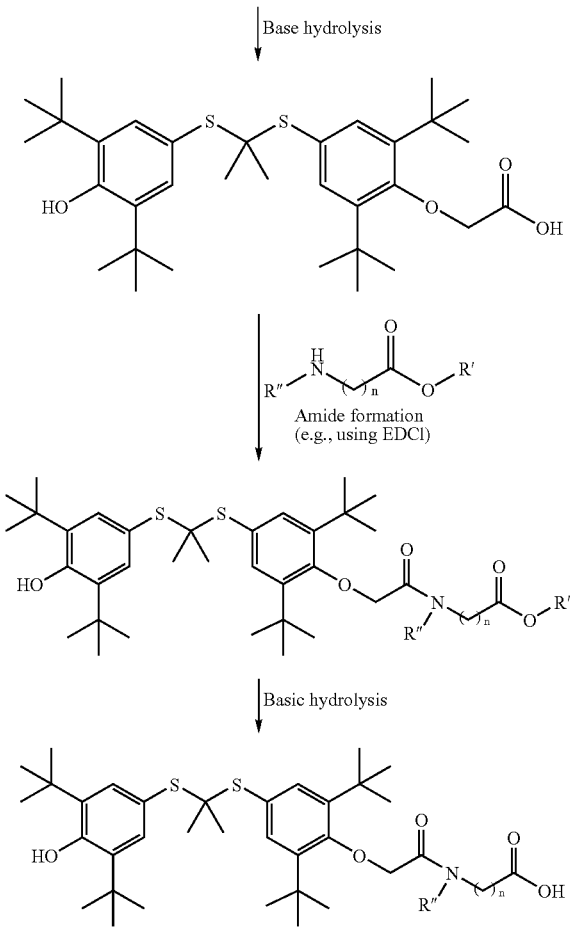

In Scheme 3, X=halide; n=1–5; R=alkyl; R'=alkyl; R"=H or alkyl

SCHEME 4

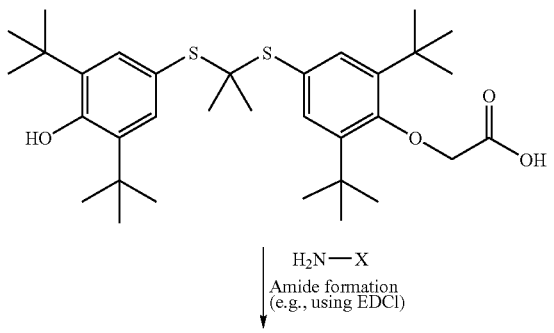

H₂N—X
Amide formation
(e.g., using EDCl)

-continued

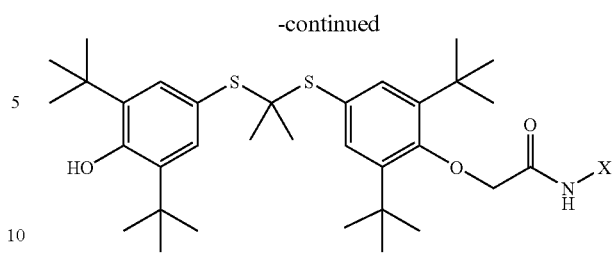

wherein X=Alkyl substituted by one or more —OH or —COOH

C. Stereoisomerism and Polymorphism

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

D. Pharmaceutically Acceptable Salt Formulations

In cases where compounds are sufficiently basic or acidic to form stable nontoxic acid or base salts, administration of the compound as a pharmaceutically acceptable salt may be appropriate. The term "pharmaceutically acceptable salts" or "complexes" refers to salts or complexes that retain the desired biological activity of the compounds of the present invention and exhibit minimal undesired toxicological effects.

Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts. Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, ethylenediamine meglumine, arginine, or lysine; or (c) combinations of (a) and (b); e.g., a zinc tannate salt or the like. Also included in this definition are pharmaceutically acceptable quaternary salts known by those skilled in the art, which specifically include the quaternary ammonium salt of the formula—$NR^+ A^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Particular FDA-approved salts can be conveniently divided between anions and cations (Approved Drug Products with Therapeutic Equivalence Evaluations (1994) U.S. Department of Health and Human Services, Public Health Service, FDA, Center for Drug Evaluation and Research, Rockville, Md.; L. D. Bighley, S. M. Berge and D. C. Monkhouse, Salt Forms of Drugs and Absorption, *Encyclopedia of Pharmaceutical Technology*, Vol. 13, J. Swarbridk and J. Boylan, eds., Marcel Dekker, N.Y. (1996)). Among the approved anions include aceglumate, acephyllinate, acetamidobenzoate, acetate, acetylasparaginate, acetylaspartate, adipate, aminosalicylate, anhydromethylenecitrate, ascorbate, aspartate, benzoate, besylate, bicarbonate, bisulfate, bitartrate, borate, bromide, camphorate, camsylate, carbonate, chloride, chlorophenoxyacetate, citrate, closylate, cromesilate, cyclamate, dehydrocholate, dihydrochloride, dimalonate, edentate, edisylate, estolate, esylate, ethylbromide, ethylsulfate, fendizoate, fosfatex, fumarate, gluceptate, gluconate, glucuronate, glutamate, glycerophosphate, glysinate, glycollylarsinilate, glycyrrhizate, hippurate, hemisulfate, hexylresorcinate, hybenzate, hydrobromide, hydrochloride, hydroiodid, hydroxybenzenesulfonate, hydroxybenzoate, hydroxynaphthoate, hyclate, iodide, isethionate, lactate, lactobionate, lysine, malate, maleate, mesylate, methylbromide, methyliodide, methylnitrate, methylsulfate, monophosadenine, mucate, napadisylate, napsylate, nicotinate, nitrate, oleate, orotate, oxalate, oxoglurate, pamoate, pantothenate, pectinate, phenylethylbarbiturate, phosphate, pacrate, plicrilix, polistirex, polygalacturonate, propionate, pyridoxylphosphate, saccharinate, salicylate, stearate, succinate, stearylsulfate, subacetate, succinate, sulfate, sulfosalicylate, tannate, tartrate, teprosilate, terephthalate, teoclate, thiocyante, tidiacicate, timonacicate, tosylate, triethiodide, triethiodide, undecanoate, and xinafoate. The approved cations include ammonium, benethamine, benzathine, betaine, calcium, carnitine, clemizole, chlorcyclizine, choline, dibenylamine, diethanolamine, diethylamine, diethylammonium diolamine, eglumine, erbumine, ethylenediamine, heptaminol, hydrabamine, hydroxyethylpyrrolidone, imadazole, meglumine, olamine, piperazine, 4-phenylcyclohexylamine, procaine, pyridoxine, triethanolamine, and tromethamine. Metallic cations include, aluminum, bismuth, calcium lithium, magnesium, neodymium, potassium, rubidium, sodium, strontium and zinc.

A particular class of salts can be classified as organic amine salts. The organic amines used to form these salts can be primary amines, secondary amines or tertiary amines, and the substituents on the amine can be straight, branched or cyclic groups, including ringed structures formed by attachment of two or more of the amine substituents. Of particular interest are organic amines that are substituted by one or more hydroxyalkyl groups, including alditol or carbohydrate moieties. These hydroxy substituted organic amines can be cyclic or acyclic, both classes of which can be primary amines, secondary amines or tertiary amines. A common class of cyclic hydroxy substituted amines are the amino sugars.

A particular class of acyclic organic amines are represented by the formula

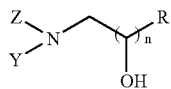

wherein Y and Z are independently hydrogen or lower alkyl or, may be taken together to form a ring, R is hydrogen, alkyl or hydroxyloweralkyl, and n is 1, 2, 3, 4, or 5. Among these hydroxylamines are a particular class characterized when n is 4. A representative of this group is meglumine, represented when Y is hydrogen, Z is methyl and R is methoxy. Meglumine is also known in the art as N-methylglucamine, N-MG, and 1-deoxy-1-(methylamino)-D-glucitol.

Pharmaceutically Acceptable Prodrugs

The invention also includes pharmaceutically acceptable prodrugs of the compounds. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase its stability.

E. Treatment of Disorders

The compounds of the present invention can be used to treat any disorder in which VCAM-1 expression is involved and/or certain redox-sensitive pro-inflammatory genes are involved such as TNFα, IL1β, MCP-1 and IL6. Such disorders include, but are not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

In one aspect of the invention, a method is provided for treating an inflammatory disease or disorder comprising administering to a patient an effective amount of a compound of the invention or a pharmaceutically acceptable salt or ester thereof.

In a particular embodiment, compounds are used for treatment of arthritis or rheumatoid arthritis. Nonlimiting examples of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout and systemic lupus erythematosus. The compounds and compositions of the invention are also suitable as disease modifying anti-rheumatoid arthritis drugs (DMARDs). The compounds and compositions also can be used for the treatment of ocular inflammation, including uveitis. In one embodiment, a method is provided for the treatment of arthritis or an arthritis related disorder including administering to a host in need thereof a compound of the invention or a pharmaceutically acceptable salt or ester thereof.

In a particular embodiment, compounds and compositions are provided for the treatment asthma, or other pulmonary inflammatory diseases. The compounds and compositions of the invention are also suitable as disease modifying anti-asthma drugs. In another embodiment, the compounds and compositions of the invention can be used to treat chronic obstructive pulmonary disease. In one aspect of the invention, a patient in need of treatment for asthma or other pulmonary inflammatory disease is provided, including administering to the patient an effective amount of a compound of the invention or a pharmaceutically acceptable salt or ester thereof.

In another embodiment, the compounds described herein are useful in both the primary and adjunctive medical treatment of cardiovascular disease. The compounds can be used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy. Compounds and compositions of the invention can be used to inhibit the progression of atherosclerosis. In one aspect of the invention, a method is provided for treating cardiovascular disorders in a patient in need thereof comprising administering to said patient an effective amount of a compound of the invention or a pharmaceutically acceptable salt thereof.

The compounds disclosed herein can be used in the treatment of inflammatory skin diseases and in particular, human endothelial disorders, which include, but are not limited to, psoriasis, dermatitis, including eczematous dermatitis, and Kaposi's sarcoma, as well as proliferative disorders of smooth muscle cells.

In yet another embodiment, the compounds disclosed herein can be selected to treat anti-inflammatory conditions in which mononuclear leucocytes are involved. Further, they can be used to treat inflammatory diseases by modulating the expression of pro-inflammatory genes such as TNFα, IL1β, IL6 and MCP-1.

In addition to inhibiting the expression of VCAM-1, some of the compounds of the invention have the additional properties of inhibiting monocyte chemoattractant protein-1 (MCP-1) and/or smooth muscle cell proliferation. MCP-1 is a chemoattractant protein produced by endothelial cells, smooth muscle cells as well as macrophages. MCP-1 promotes integrin activation on endothelial cells thereby facilitating adhesion of leukocytes to VCAM-1, and MCP-1 is a chemoattractant for monocytes. MCP-1 has been shown to play a role in leukocyte recruitment in a number of chronic inflammatory diseases including atherosclerosis, rheumatoid arthritis, and asthma. Its expression is upregulated in these diseases and as such inhibition of MCP-1 expression represents a desirable property of anti-inflammatory therapeutics. Furthermore, smooth muscle cell hyperplasia and resulting tissue remodeling and decreased organ function is yet another characteristic of many chronic inflammatory diseases including atherosclerosis, chronic transplant rejection and asthma. Inhibition of the hyperproliferation of smooth muscle cells is another desirable property for therapeutic compounds.

Cytokines are extracellular signaling proteins produced by many cell types playing a central role in human immune response, and can be categorized as either pro-inflammatory or anti-inflammatory in action. TNF-α, IL-1β and IL-6 are major pro-inflammatory cytokines implicated in the pathogenesis of numerous diseases. The expression of these proinflammatory cytokines is also redox-regulated (Haddad, J. J.; Saade, N. E.; Safieh-Garabedian, B. Redox regulation of TNF-α Biosynthesis: Augmentation by Irreversible Inhibition of γ-Glutamylcysteine Synthetase and the Involvement of an IκB-α/NF-κB-independent Pathway in Alveolar Epithelial Cells. *Cell Signal.* 2002, 14, 211–218).

In another embodiment, the compounds of the present invention can be selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. They are also indicated for the prevention or treatment of graft-versus-host disease, which sometimes occurs following bone marrow transplantation.

In another aspect of the invention, the compounds can be used in compositions, including pharmaceutical compositions or a pharmaceutically acceptable salt thereof and/or a pharmaceutically acceptable carrier.

The compounds, methods and compositions can be used alone or as adjunct or combination therapy simultaneously or in series.

F. Combination and Alternation Therapy

Any of the compounds disclosed herein can be administered in combination or alternation with a second biologically active agent to increase its effectiveness against the target disorder.

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The efficacy of a drug can be prolonged, augmented, or restored by administering the compound in combination or alternation with a second, and perhaps third, agent that induces a different biological pathway from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the condition.

Any method of alternation can be used that provides treatment to the patient. Nonlimiting examples of alternation patterns include 1–6 weeks of administration of an effective amount of one agent followed by 1–6 weeks of administration of an effective amount of a second agent. The alternation schedule can include periods of no treatment. Combination therapy generally includes the simultaneous administration of an effective ratio of dosages of two or more active agents.

Illustrative examples of specific agents that can be used in combination or alternation with the compounds of the present invention are described below in regard to asthma and arthritis. The agents set out below or others can alternatively be used to treat a host suffering from any of the other disorders listed above or that involve VCAM-1 or MCP-1. Illustrative second biologically active agents for the treatment of cardiovascular disease are also provided below.

i) Asthma

In one embodiment, the compounds of the present invention are administered in combination or alternation with heparin, frusemide, ranitidine, an agent that effects respiratory function, such as DNAase, or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-D$_4$-receptor antagonists such as Accolate (zafirlukast), Ziflo (zileuton), leukotriene C$_1$ or C$_2$ antagonists and inhibitors of leukotriene synthesis such as zileuton for the treatment of asthma, or an inducible nitric oxide synthase inhibitor.

In another embodiment, the active compound is administered in combination or alternation with one or more other prophylactic agent(s). Examples of prophylactic agents that can be used in alternation or combination therapy include but are not limited to sodium cromoglycate, Intal (cromolyn sodium, Nasalcrom, Opticrom, Crolom, Ophthalmic Crolom), Tilade (nedocromil, nedocromil sodium) and ketotifen.

In another embodiment, the active compound is administered in combination or alternation with one or more other β$_2$-adrenergic agonist(s) (β agonists). Examples of β$_2$-adrenergic agonists (β agonists) that can be used in alternation or combination therapy include but are not limited to albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, pseudoephedrine (pseudoephedrine polixtirex, pseudoephedrine tannate, pseudoephedrine hydrochloride, pseudoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other antihistimine(s) ($H_1$ receptor antagonists). Examples of antihistimines ($H_1$ receptor antagonists) that can be used in alternation or combination therapy include alkylamines, ethanolamines ethylenediamines, piperazines, piperidines or phenothiazines. Some non-limiting examples of antihistimes are Chlortrimeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphen-hydramine), Tavist (clemastine), Dimetabs (dimenhydrinate, Dramamine, Marmine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

Alternatively, the compound of the present invention may be administered in combination or alternation with
(a) xanthines and methylxanthines, such as Theo-24 (theophylline, Slo-Phylline, Uniphyllin, Slobid, Theo-Dur), Choledyl (oxitriphylline), aminophylline;
(b) anticholinergic agents (antimuscarinic agents) such as belladonna alkaloids, Atrovent (ipratropium bromide), atropine, oxitropium bromide;
(c) phosphodiesterase inhibitors, including phosphodiesterase IV inhibitors such as zardaverine;
(d) calcium antagonists such as nifedipine;
(e) potassium activators such as cromakalim for the treatment of asthma;
(f) B-eotaxin chemokine receptor, CCR3, antagonists; or
(g) IL-5 antibodies, IL-13 antibodies, IL-13 antagonists, IL-4 receptor antagonists, and IgE antibodies (Xolair).

ii) Arthritic disorders

In one embodiment, the compound of the present invention can also be administered in combination or alternation with apazone, amitriptyline, chymopapain, collegenase, cyclobenzaprine, diazepam, fluoxetine, pyridoxine, ademetionine, diacerein, glucosamine, hylan (hyaluronate), misoprostol, paracetamol, superoxide dismutase mimics, IL-1 receptor antagonists, IL-2 receptor antagonists, IL-6 receptor antagonists, TNFα receptor antagonists, TNFα antibodies, P38 MAP Kinase inhibitors, tricyclic antidepressants, cJun kinase inhibitors or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, MAP-KAPK2 (MK2) Kinase inhibitors, Chemokine Receptor Antagonists such as CCR5 Receptor antagonists, Interleukin Converting Enzyme (ICE) inhibitors, IKB Kinase (IKK1, IKK2) inhibitors, TNF-α Convertase Enzyme (TACE) inhibitors, ICK Kinase inhibitors, Janus Kinase 3 (JAK3) inhibitors, Kinase insert domain-containing Receptor (KdR) Kinase inhibitors, and inducible nitric oxide sythase (iNOS) inhibitors.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib), Bextra (valdecoxib), Dynastat (parecoxib sodium) and Vioxx (rofacoxib). Some non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Ahninoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine, Hydrochloride, Bomyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Momiflumate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

iii) Cardiovascular Disease

Compounds useful for combining with the compounds of the present invention for the treatment of cardiovascular disease encompass a wide range of therapeutic compounds.

Ileal bile acid transporter (IBAT) inhibitors, for example, are useful in the present invention, and are disclosed in patent application no. PCT/US95/10863, herein incorporated by reference. More IBAT inhibitors are described in PCT/US97/04076, herein incorporated by reference. Still further IBAT inhibitors useful in the present invention are described in U.S. application Ser. No. 08/816,065, herein incorporated by reference. More IBAT inhibitor compounds useful in the present invention are described in WO 98/40375, and WO 00/38725, herein incorporated by reference. Additional IBAT inhibitor compounds useful in the present invention are described in U.S. application Ser. No. 08/816,065, herein incorporated by reference.

In another aspect, the second biologically active agent is a statin. Statins lower cholesterol by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol (Grundy, S. M. *New Engl. J. Med.* 319, 24 (1988); Endo, A. *J. Lipid Res.* 33, 1569 (1992)). Depending on the agent and the dose used, statins may decrease plasma triglyceride levels and may increase HDLc. Currently the statins on the market are lovastatin (Merck), simvastatin (Merck), pravastatin (Sankyo and Squibb) and fluvastatin (Sandoz). A fifth statin, atorvastatin (Parke-Davis/Pfizer), is the most recent entrant into the statin market. Any of these statins can be used in combination with the compounds of the present invention.

MTP inhibitor compounds useful in the combinations and methods of the present invention comprise a wide variety of structures and functionalities. Some of the MTP inhibitor compounds of particular interest for use in the present invention are disclosed in WO 00/38725, the disclosure from which is incorporated by reference. Descriptions of these therapeutic compounds can be found in *Science,* 282, 23 October 1998, pp. 751–754, herein incorporated by reference.

Cholesterol absorption antagonist compounds useful in the combinations and methods of the present invention comprise a wide variety of structures and functionalities. Some of the cholesterol absorption antagonist compounds of particular interest for use in the present invention are described in U.S. Pat. No. 5,767,115, herein incorporated by reference. Further cholesterol absorption antagonist compounds of particular interest for use in the present invention, and methods for making such cholesterol absorption antagonist compounds are described in U.S. Pat. No. 5,631,365, herein incorporated by reference.

A number of phytosterols suitable for the combination therapies of the present invention are described by Ling and Jones in "Dietary Phytosterols: A Review of Metabolism, Benefits and Side Effects," *Life Sciences,* 57 (3), 195–206 (1995). Without limitation, some phytosterols of particular use in the combination of the present invention are Clofibrate, Fenofibrate, Ciprofibrate, Bezafibrate, Gemfibrozil. The structures of the foregoing compounds can be found in WO 00/38725.

Phytosterols are also referred to generally by Nes (*Physiology and Biochemistry of Sterols*, American Oil Chemists' Society, Champaign, Ill., 1991, Table 7-2). Especially preferred among the phytosterols for use in the combinations of the present invention are saturated phytosterols or stanols. Additional stanols are also described by Nes (Id.) and are useful in the combination of the present invention. In the combination of the present invention, the phytosterol preferably comprises a stanol. In one preferred embodiment the stanol is campestanol. In another preferred embodiment the stanol is cholestanol. In another preferred embodiment the stanol is clionastanol. In another preferred embodiment the stanol is coprostanol. In another preferred embodiment the stanol is 22,23-dihydrobrassicastanol. In another embodiment the stanol is epicholestanol. In another preferred embodiment the stanol is fucostanol. In another preferred embodiment the stanol is stigmastanol.

Another embodiment the present invention encompasses a therapeutic combination of a compound of the present invention and an HDLc elevating agent. In one aspect, the second HDLc elevating agent can be a CETP inhibitor such as Pfizer's Torcetrapib or a combination of a CETP inhibitor and a statin, i.e., Torcetrapib and Atorvastatin. Individual CETP inhibitor compounds useful in the present invention are separately described in WO 00/38725, the disclosure of which is herein incorporated by reference. Other individual CETP inhibitor compounds useful in the present invention are separately described in WO 99/14174, EP818448, WO 99/15504, WO 99/14215, WO 98/04528, and WO 00/17166, the disclosures of which are herein incorporated by reference. Other individual CETP inhibitor compounds useful in the present invention are separately described in WO 00/18724, WO 00/18723, and WO 00/18721, the disclosures of which are herein incorporated by reference. Other individual CETP inhibitor compounds useful in the present invention are separately described in WO 98/35937 as well as U.S. Pat. Nos. 6,313,142, 6,310,075, 6,197,786, 6,147,090, 6,147,089, 6,140,343, and 6,140,343, the disclosures of which is herein incorporated by reference.

In another aspect, the second biologically active agent can be a fibric acid derivative. Fibric acid derivatives useful in the combinations and methods of the present invention comprise a wide variety of structures and functionalities which have been reported and published in the art.

The compounds of the present invention may also be used in combination or alternation therapy with PPAR agonists including PPARα/γ dual agonists, PPARα agonists, and PPARγ agonists.

In another embodiment the present invention encompasses a therapeutic combination of a compound of the present invention and an antihypertensive agent. Hypertension is defined as persistently high blood pressure. In another embodiment, the compound is administered in combination with an ACE inhibitor, a beta andrenergic blocker, alpha andrenergic blocker, angiotensin II receptor antagonist, vasodilator and diuretic.

G. Pharmaceutical Compositions

Any host organism, including a patient, mammal, and specifically a human, suffering from any of the above-described conditions can be treated by the administration of a composition comprising an effective amount of the compound of the invention or a pharmaceutically acceptable salt thereof, optionally in a pharmaceutically acceptable carrier or diluent.

The composition can be administered in any desired manner, including oral, topical, parenteral, intravenous, intradermal, intra-articular, intra-synovial, intrathecal, intra-arterial, intracardiac, intramuscular, subcutaneous, intraorbital, intracapsular, intraspinal, intrastemal, topical, transdermal patch, via rectal, vaginal or urethral suppository, peritoneal, percutaneous, nasal spray, surgical implant, internal surgical paint, infusion pump, or via catheter. In one embodiment, the agent and carrier are administered in a slow release formulation such as an implant, bolus, microparticle, microsphere, nanoparticle or nanosphere. For standard information on pharmaceutical formulations, see Ansel, et al., *Pharmaceutical Dosage Forms and Drug Delivery Systems*, Sixth Edition, Williams & Wilkins (1995).

An effective dose for any of the herein described conditions can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. Typical systemic dosages for all of the herein described conditions are those ranging from 0.1 mg/kg to 500 mg/kg of body weight per day as a single daily dose or divided daily doses. Preferred dosages for the described conditions range from 5–1500 mg per day. A more particularly preferred dosage for the desired conditions ranges from 25–750 mg per day. Typical dosages for topical application are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

For example, the compound can be in the form of a dosage unit including about 0.5–1000 mg of compound, e.g., in a tablet or capsule.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The compound can also be mixed with other active materials that do not impair the desired action, or with materials that supplement the desired action. The compounds can also be administered in combination with non-steroidal antiinflammatories such as ibuprofen, indomethacin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline, bacteriostatic water, Cremophor EL™ (BASF, Parsippany, N.J.) or phosphate buffered saline (PBS).

In one form, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Any of the compounds described herein for combination or alternation therapy can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound. This can easily be assessed by preparing the derivative and testing its anti-inflammatory activity according to known methods.

The following examples are understood to be illustrative only and are not intended to limit the scope of the present invention in any way.

EXAMPLES

Intermediates and final products were characterized by conventional proton NMR, mass spectral analyses and standard analytical methods known to those skilled in the art.

Example 1

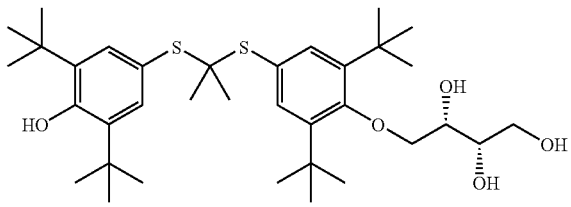

4-{2,6-Di-tert-butyl-4-[1-(3,5-di-tert-butyl-4-hydroxyphenylsulfanyl)-1-methylethyl-sulfanyl]phenoxy}butane-1,2(S),3(S)-triol Ex-1A

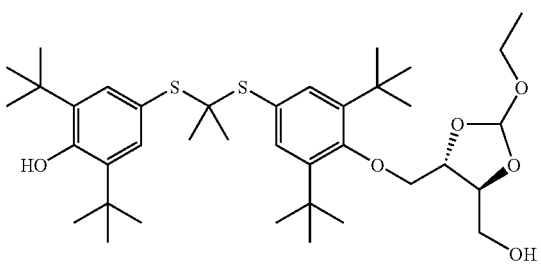

To a solution of probucol (5.16 g, 10 mmol) in THF (20 mL) cooled to 0° C. were added triphenylphosphine (1.3 g, 5 mmol), diethyl azodicarboxylate (0.8 mL g, 5 mmol) and 2-ethoxy-1,3-dioxolane-4(S),5(S)-dimethanol (0.89 g, 5 mmol; Nicolaou, K. C. et al.: J. Org. Chem. 1985, 50, 1440–1456). The resultant mixture was stirred at reflux for 3 hours and then evaporated. Silica gel chromatography (hexanes/ethyl acetate 4:1) gave 2,6-di-tert-butyl-4-{1-[3,5-di-tert-butyl-4-(2-ethoxy-5(S)-hydroxymethyl[1,3]dioxolan-4(S)-yl-methoxy)-phenylsulfanyl]-1-methyl-ethylsulfanyl}-phenol in three parts: diasteroisomer A (0.36 g), diastereoisomer B (0.22 g) and a mixture of the two (0.72 g) all as viscous residues (total yield: 39%). Diasteroisomer A: $^1$H-NMR (CDCl$_3$) δ 7.56 (s, 2H, Ph-H), 7.44 (s, 2H, Ph-H), 5.89 [s, 1H, CH(O)$_3$], 5.37 (s, 1H, PhOH), 4.734.81 (m, 1H, PhOCH$_2$CH), 4.194.25 (m, 1H, CHCH$_2$OH), 3.8 04.01 (m, 3H, CH$_2$), 3.623.96 (m, 3H, CH$_2$O), 2.80 (dd, J=9, 3, 1H, OH), 1.45 (s, 6H, S,S'-isopropylidene), 1.44 (s, 18H, tert-butyls), 1.43 (s, 18H, tert-butyls), 1.25 (t, 3H, OCH$_2$CH$_3$). Diastereoisomer B: $^1$H-NMR (CDCl$_3$) δ 7.56 (s, 2H, Ph-H), 7.44 (s, 2H, Ph-H), 5.92 [s, 1H, CH(O)$_3$], 5.36 (s, 1H, PhOH), 4.504.59 (m, 1H, PhOCH$_2$CH), 4.134.30 (m, 3H, CHCH$_2$OH, CH$_2$O), 3.894.00 (m, 3H, CH$_2$O), 3.61 (quad, J=7, 2H, OCH$_2$CH$_3$), 1.86 (dd, J=6, 8, 1H, OH), 1.4 11.46 (m, 42H, S,S'-isopropylidene, tert-butyls), 1.21 (t, 3H, OCH$_2$CH$_3$).

The mixture obtained from Ex-1A (0.72 g, 1.1 mmol) was dissolved in methanol (25 mL). Acetic acid (2 mL) and water (1 mL) were added and the resultant mixture was stirred at reflux for 3 hours and then evaporated to about 10 mL. It was poured into water (100 mL) and extracted with dichloromethane (2×100 mL). The organic phase was dried over magnesium sulfate and evaporated. The residue was dissolved in methanol (15 mL) and potassium carbonate (0.5 g) was added. The mixture was stirred at room temperature for 1 hour and then poured into 1 N HCl solution (100 mL). It was extracted with dichloromethane (2×100 mL), dried over magnesium sulfate, and evaporated. Silica gel chromatography (dichloromethane/ethyl acetate 4:1) gave 4-{2,6-Di-tert-butyl-4-[1-(3,5-di-tert-butyl-4-hydroxyphenylsulfanyl)-1-methylethyl-sulfanyl]phenoxy}butane-1,2(S),-3 (s)-triol as a white powder (0.45 g, 66%), mp 69–71° C. $^1$H-NMR (CDCl$_3$) δ 7.56 (s, 2H, Ph-H), 7.45 (s, 2H, Ph-H), 5.36 (s, 1H, PhOH), 4.264.34 (m, 1H, PhOCH$_2$CH), 4.01 (dd, J=9, 10, 1H, CH—O—), 3.723.86 (m, 4H, , CH—O—), 2.692.77 (m, 2H, OH), 2.15 (br. t, 1H, OH), 1.421.47 (m, 42H, S,S'-isopropylidene, tert-butyls). MS m/z: 643 ([M+Na]+, 100%). Anal. calcd. for C$_{35}$H$_{256}$O$_5$S$_2$: C67.70, H9.09, S10.33; found: C67.33, H9.02, S10.03.

Example 2

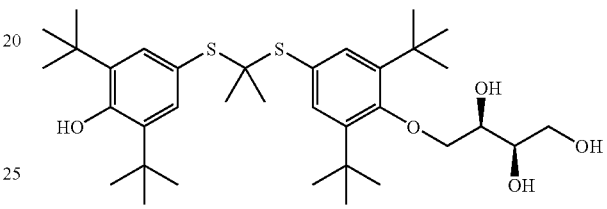

4-{2,6-Di-tert-butyl-4-[1-(3,5-di-tert-butyl-4-hydroxyphenylsulfanyl)-1-methylethylsulfanyl]phenoxy}butane-1,2(R),3(R)-triol The title compound was prepared using the same procedure as described in Ex-1 starting from probucol and 2-ethoxy-1,3-dioxolane-4(R),5(R)-dimethanol. White solid, mp 69–71° C. $^1$H-NMR (CDCl$_3$) δ 7.56 (s, 2H, Ph-H), 7.45 (s, 2H, Ph-H), 5.38 (s, 1H, PhOH), 4.254.32 (m, 1H, PhOCH$_2$CH), 3.96 (dd, J=9, 10, 1H, CH—O—), 3.723.86 (m, 4H, , CH—O—), 3.003.40 (m, 3H, OH), 1.46 (s, 6H, S,S'-isopropylidene), 1.45 (s, 18H, tert-butyls), 1.43 (s, 18H, tert-butyls). MS m/z: 643 ([M+Na]$^+$, 100%). Anal. calcd. for C$_{35}$H$_{56}$O$_5$S$_2$.⅓H$_2$O: C67.05, H9.11, S, 10.23; found: C67.03, H9.06, S10.01.

Example 3

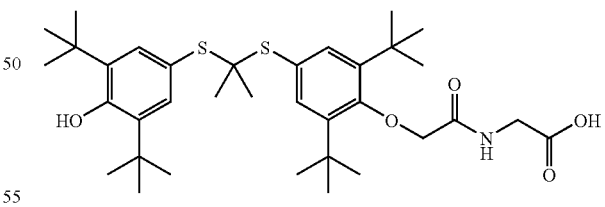

(2-{2,6-Di-tert-butyl-4-[1-(3,5-di-tert-butyl-4-hydroxyphenylsulfanyl)-1-methylethylsulfanyl]phenoxy}acetylamino)acetic acid

Example 3A

To a solution of probucol (0.5 g, 0.97 mmol) in dimethylformamide (1.5 mL) were added ethyl iodoacetate (0.31 g, 1.45 mmol) and 40% potassium fluoride on alumina (0.7 g, 4.8 mmol). The mixture was stirred for 24 hours and then diluted with ether (25 mL), filtered and washed with water (2×5 mL). The ether layer was dried over MgSO₄, filtered and concentrated. Silica gel chromatography (hexanes/ether 5:95) yielded 160 mg of {2,6-di-tert-butyl-4-[1-(3,5-di-tert-butyl-4-hydroxy-phenylsulfanyl)-1-methyl-ethylsulfanyl]-phenoxy}-acetic acid ethyl ester which was used directly for the next step of reaction.

Example 3B

{2,6-Di-tert-butyl-4-[1-(3,5-di-tert-butyl-4-hydroxy-phenylsulfanyl)-1-methyl-ethylsulfanyl]-phenoxy}-acetic acid ethyl ester (Ex-3A, 160 mg) was dissolved in THF/H₂O/MeOH (4:1:1) (4 mL) and lithium hydroxide hydrate (50 mg) was added. The resultant mixture was stirred for 1 h and then neutralized with 1N HCl. It was extracted with ether (2×10 mL), dried over MgSO₄, filtered, and concentrated. Silica gel chromatography (hexanes/ether 50:50) gave acetic acid, [4-[[1-[[3,5-bis(1,1-dimethylethyl)-4-hydroxyphenyl]thio]-1-methylethyl]thio]-2,6-bis(1,1-dimethylethyl)-phenoxy]as a white solid (90 mg, 16%), mp 164–165° C. ¹H-NMR (CDCl₃) δ 7.55 (s, 2H, Ph-H), 7.40 (s, 2H, Ph-H), 5.35 (s, 1H, Ph-OH), 4.40 (s, 2H, OCH₂COOH), 1.43 (s, 6H, S,S'-isopropylidene), 1.41 (s, 9H, tert-butyl), 1.39 (s, 9H, tert-butyl). MS m/z: 613 ([M+K]⁺, 60%), 159 (100%). Anal. calcd. for C₃₃H₅₀O₄S₂: C68.95, H8.77, S11.15, found: C68.67, H8.72, S11.09.

Example 3C

To a solution of acetic acid, [4-[[1-[[3,5-bis(1,1-dimethylethyl)-4-hydroxyphenyl]thio]-1-methylethyl]thio]-2,6-bis(1,1-dimethylethyl)phenoxy]-(Ex-3B, 50 mg, 0.087 mmol) in methylene chloride (0.87 mL) were added glycine ethyl ester hydrochloride (15.8 mg, 0.11 mmol), 1-(3-dimethylaminopropyl-3-ethyl carbodiimide hydrochloride (22 mg, 0.11 mmol) and 4-dimethylaminopyridine (28 mg, 0.23 mmol). The reaction mixture was stirred overnight and then the methylene chloride evaporated. The reaction was diluted with ether (10 mL) and washed with water (2×3 mL), dried over MgSO₄, filtered, and concentrated. The crude mixture was purified by silica gel chromatography (ether/hexanes 50:50) to give 50 mg of (2-{2,6-di-tert-butyl-4-[1-(3,5-di-tert-butyl-4-hydroxy-phenylsulfanyl)-1-methyl-ethylsulfanyl]-phenoxy}-acetylamino)-acetic acid ethyl ester which as used directly for the next step of reaction.

(2-{2,6-Di-tert-butyl-4-[1-(3,5-di-tert-butyl-4-hydroxy-phenylsulfanyl)-1-methyl-ethyl-sulfanyl]-phenoxy}-acetylamino)-acetic acid ethyl ester (Ex-3C, 50 mg) was dissolved in THF/H₂O/MeOH (2:1:1, 1 mL), lithium hydroxide monohydrate (15 mg, 0.36 mmol) was added, and the reaction stirred for 1 h. The reaction was neutralized with 1N HCl and extracted with ether (2×10 mL), dried over MgSO₄, filtered, and concentrated to give the title product as a viscous residue (25 mg, 45%) which solidified, mp 91–94° C. ¹H-NMR (CDCl₃) δ 7.56 (s, 2H, Ph-H), 7.42 (s, 2H, Ph-H), 7.28 (t, 1H, NH), 5.39 (br s, 1H, Ph-OH), 4.31 [s, 2H, OCH₂C(O)], 4.22 (d, J=5.2 Hz, 2H, NHCH₂—COOH), 1.44 (s, 6H, S,S'-isopropylidene), 1.42 (s, 18H, tert-butyls), 1.39 (s, 18H, tert-butyls). MS m/z: 654 ([M+Na]⁺, 100%). Anal. calcd. for C₃₅H₅₃NO₅S₂: C66.52, H8.45, N2.22, S10.14; found: C66.23, H8.30, N2.23, S9.98.

Example 4

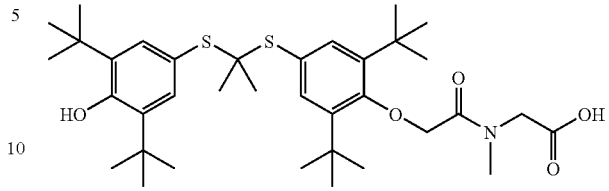

[(2-{2,6-Di-tert-butyl-4-[1-(3,5-di-tert-butyl-4-hydroxyphenylsulfanyl)-1-methylethylsulfanyl] phenoxy}acetyl)methylamino]acetic acid The title compound was prepared in a similar procedure as described in Ex-3 starting from acetic acid, [4-[[1-[[3,5-bis(1,1-dimethylethyl)-4-hydroxyphenyl]thio]-1-methylethyl]thio]-2,6-bis(1,1-dimethylethyl)phenoxy]- (Ex-3B) and sarcosine ethyl ester. Off-white solid, mp 115–119° C. ¹H-NMR (CDCl₃) δ 7.58 (s, 2H, Ph-H), 7.45 (s, 2H, Ph-H), 5.37 (s, 1H, Ph-OH), 4.52 (s, 2H, PhOCH₂), 4.24 (s, 2H, NCH₂), 3.03 (s, 3H, NCH₃), 1.47 (s, 6H, S,S'-isopropylidene), 1.44 (s, 18H, tert-butyls), 1.43 (s, 18H, tert-butyls). MS m/z: 668 ([M+Na]⁺, 100%). Anal. calcd. for C₃₆H₅₅NO₅S₂: C66.94, H9.58, N2.17, S9.93; found: C67.13, H8.58, N2.20, S9.79.

Example 5

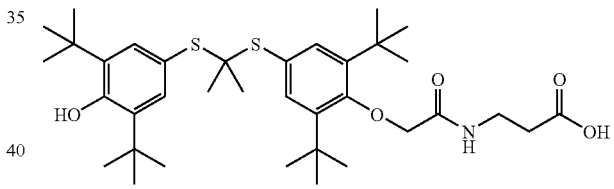

3-(2-{2,6-Di-tert-butyl-4-[1-(3,5-di-tert-butyl-4-hydroxyphenylsulfanyl)-1-methylethylsulfanyl] phenoxy}acetylamino)propionic acid Example 5A 3-(2-{2,6-Di-tert-butyl-4-[1-(3,5-di-tert-butyl-4-hydroxyphenylsulfanyl)-1-methylethylsulfanyl] phenoxy}acetylamino)propionic acid ethyl ester was prepared in a similar procedure as described in Ex-3C starting from acetic acid, [4-[[1-[[3,5-bis(1,1-dimethylethyl)-4-hydroxyphenyl]thio]-1-methylethyl]thio]-2,6-bis(1,1-dimethylethyl)-phenoxy]-(Ex-3B) and ethyl 3-aminobutyrate. Off-white solid, mp 116–117° C. ¹H-NMR (CDCl₃) δ 7.56 (s, 2H, Ph-H), 7.43 (s, 2H, Ph-H), 7.31 (t, J=6, 1H, NH), 5.37 (s, 1H, Ph-OH), 4.24 (s, 2H, PhOCH₂), 4.17 (quad, J=7, 2H, OCH₂CH₃), 3.69 (quad, J=6, 2H, NHCH₂), 2.61 (t, J=6, NHCH₂CH₂), 1.45 (s, 6H, S,S'-isopropylidene), 1.44 (s, 18H, tert-butyls), 1.39 (s, 18H, tert-butyls), 1.28 (t, J=7, 3H, OCH₂CH₃). MS m/z: 696 ([M+Na]⁺, 100%). Anal. calcd. for C₃₈H₅₉NO₅S₂: C67.72, H8.82, N2.08; found: 67.67, H8.83, N2.04.

The title compound was prepared in a similar procedure as described in Ex-3 by hydrolyzing 3-(2-{2,6-di-tert-butyl- 4-[1-(3,5-di-tert-butyl-4-hydroxyphenylsulfanyl)-1-methyl-ethylsulfanyl]phenoxy}acetylamino)propionic acid ethyl ester (Ex-5A). Off-white solid, mp 183–184° C. $^1$H-NMR (CDCl$_3$) δ 7.56 (s, 2H, Ph-H), 7.43 (s, 2H, Ph-H), 7.33 (t, J=6, 1H, NH), 5.37 (s, 1H, Ph-OH), 4.25 (s, 2H, PhOCH$_2$), 4.69 (quad, J=6, 2H, NHCH$_2$), 2.68 (t, J=6, NHCH$_2$CH$_2$), 1.45 (s, 6H, S,S'-isopropylidene), 1.44 (s, 18H, tert-butyls), 1.38 (s, 18H, tert-butyls). MS m/z: 668 ([M+Na]$^+$, 100%). Anal. calcd. for C$_{36}$H$_{55}$NO$_5$S$_2$: C66.94, H8.58, N2.17; found: 67.10, H8.62, N2.03.

Example 6

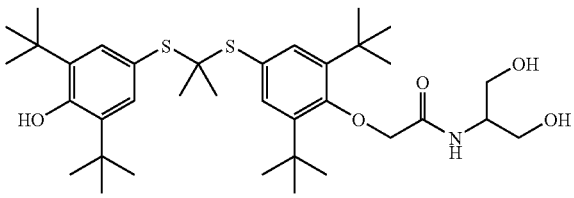

2-{2,6-Di-tert-butyl-4-[1-(3,5-di-tert-butyl-4-hydroxyphenylsulfanyl)-1-methyl-ethylsulfanyl]phenoxy}-N-(2-hydroxy-1-hydroxymethyl-ethyl)acetamide To a solution of acetic acid, [4-[[1-[[3,5-bis(1,1-dimethylethyl)-4-hydroxyphenyl]-thio]-1-methylethyl]thio]-2,6-bis(1,1-dimethylethyl)phenyl]-(Ex-3B, 4.87 g, 8.49 mmol) in dichloromethane (200 mL) was added serinol (0.77 g, 8.49 mmol) and 1-(3-dimethylaminopropyl)-3-ethylcarbodiimide hydrochloride (3.26 g, 17 mmol), and the mixture was stirred at rt overnight. It was poured into water (100 ml) and the organic phase was dried over magnesium sulfate and evaporated. Silica gel chromatography (hexanes/ethyl acetate 1:2) gave the title compound as a white solid (2.95 g, 57%), mp 163–164° C. $^1$H-NMR (CDCl$_3$) δ 7.57 (s, 2H, Ph-H), 7.49 (d, J=7, 1H, NH), 7.44 (s, 2H, Ph-H), 5.37 (s, 1H, Ph-OH), 4.28 (s, 2H, PhOCH$_2$), 4.10̃4.29 (m, 1H, NHCH), 3.8̃24.00 (m, 4H, CH$_2$OH), 1.45 (s, 6H, S,S'-isopropylidene), 2.44 (dd, J=6, 11, 2H, OH), 1.44 (s, 18H, tert-butyls), 1.41 (s, 18H, tert-butyls). MS m/z: 670 ([M+Na]$^+$, 100%). Anal. calcd. for C$_{36}$H$_{57}$NO$_5$S$_2$: C66.73, H8.87, N2.16 S9.90; found: C66.37, H8.90, N2.24, S9.92.

Example 7 and Example 8

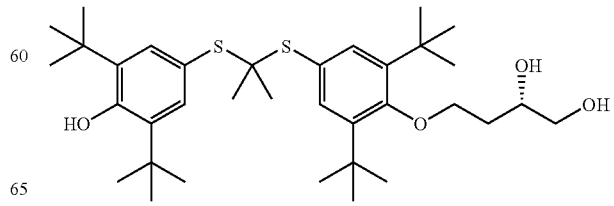

4-{2,6-Di-tert-butyl-4-[1-(3,5-di-tert-butyl-4-hydroxyphenylsulfanyl)-1-methylethylsulfanyl]-phenoxy}butane-1,2(S),3(R)-triol

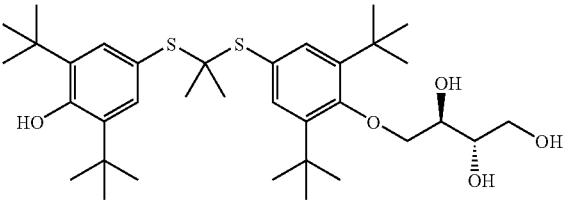

4-{2,6-Di-tert-butyl-4-[1-(3,5-di-tert-butyl-4-hydroxyphenylsulfanyl)-1-methylethylsulfanyl]-phenoxy}butane-1,2(R),3(S)-triol The title compounds can be prepared using the same procedure as described in Ex-1 starting from probucol and 2-ethoxy-1,3-dioxolane-4(S),5(R)-dimethanol and performing a chiral separation.

Example 9

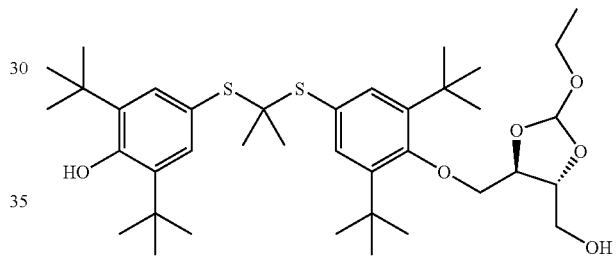

2,6-Di-tert-butyl-4-{1-[3,5-di-tert-butyl-4-(2-ethoxy-5(R)-hydroxymethyl-[1,3]dioxolan-4(R)-yl-methoxy)-phenylsulfanyl]-1-methyl-ethylsulfanyl}-phenol The title compound was prepared using the same procedure as described in Ex-1A starting from probucol and 2-ethoxy-1,3-dioxolane-4(R),5(R)-dimethanol as a white solid (10.3 g, 35%), mp 60–62° C. $^1$H-NMR (300 MHz, CDCl$_3$) δ 7.56 (s, 2H), 7.44 (s, 2H), 5.89 (s, 1H), 5.36 (s, 1H), 4.75–4.78 (m, 1H), 4.19–4.24 (m, 2H), 3.92–3.99 (m, 2H), 3.84 (dd, 1H, J=10.0, 4.2 Hz), 3.60–3.74 (m, 2H), 2.79 (dd, 1H, J=9.1, 3.3 Hz). 1.43–1.45 (m, 42H), 1.28 (t, 3H, J=7.2 Hz). HRMS (ESI) calcd for C$_{38}$H$_{60}$O$_6$S$_2$ (M+Na), 699.3729; found, 699.3756. Anal. calcd. for C$_{38}$H$_{60}$O$_6$S$_2$: C, 67.42, H, 8.93, S, 9.47; found: C, 67.04, H, 9.00, S, 8.86.

Example 10

4-{2,6-Di-tert-butyl-4-[1-(3,5-di-tert-butyl-4-hydroxy-phenylsulfanyl)-1-methyl-ethylsulfanyl]-phenoxy}-butane-1,2(S)-diol

Ex-10A

A 500 mL round bottom flask equipped with a nitrogen adapter and a temperature probe was charged with 10.0 g (57 mmol, 1 eq) of (S)-(+)-2,2-dimethyl-5-oxo-1,3-dioxolane-4-acetic acid and 35 mL of anhydrous THF. The solution was cooled to 0° C. using an ice bath and 75 mL (75 mmol, 1.3 eq) of 1.0 M borane in THF was slowly charged. Upon complete addition, the flask was slowly warmed to ambient temperature and consumption of starting material was monitored by TLC. After stirring for 3 hours, starting material was consumed and the flask was cooled to 0° C. and quenched by the slow addition of 50 mL of methanol. The resulting solution was concentrated under reduced pressure at 25° C. The residue was dissolved in 100 mL of methanol and concentrated under reduced pressure at 25° C. The residue was dissolved in 100 mL of EtOAc and concentrated under reduced pressure and the clear oil was dried in vacuo to yield 9.3 g (58 mmol, 100% yield) of (S)-(+)-2,2-dimethyl-5-oxo-1,3-dioxolane-4-ethanol as clear colorless oil. $^1$H NMR (300 MHz, CDCl$_3$) δ 4.58 (dd, J=5.03 and 7.49 Hz, 1H), 3.82–3.88 (m, 2H), 2.13–2.20 (m, 1H), 1.96–2.07 (m, 1H), 1.64 (s, 3H), 1.57 (s, 1H).

Ex-10B

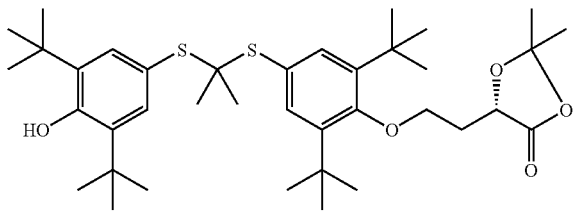

A 1 L round bottom flask equipped with a nitrogen adapter, temperature probe and addition funnel was charged with 9.3 g (58 mmol, 1.3 eq) of (s)-(+)-2,2-dimethyl-5-oxo-1,3-dioxolane-4-ethanol (Ex-10A), 500 mL of anhydrous THF, 25.6 g (98.3 mmol, 2.2 eq) of triphenylphosphine and 23.1 g (44.7 mmol, 1 eq) of probucol. The reaction mixture was cooled to 0° C. with an ice bath, 14.0 mL (89.4 mmol, 2.0 eq) of diethyl azodicarboxylate was charged to the addition funnel and then added dropwise to the reaction mixture. The dark reaction mixture was warmed to ambient temperature and stirred for 18 hours. The reaction mixture concentrated under reduced pressure and the residue was purified by silica gel chromatography (2% EtOAc/hexanes gradient to 5% EtOAc/hexanes) to yield 8.2 g of 2,6-di-tert-butyl-4-(1-{3,5-di-tert-butyl-4-[2-(2,2-dimethyl-[1,3]dioxolan-4(S)-yl)-ethoxy]-phenylsulfanyl}-1-methyl-ethylsulfanyl)-phenol as a white solid, mp 44–46° C. $^1$H NMR (300 MHz, CDCl$_3$) δ: 7.56 (s, 2H), 7.47 (s, 2H), 5.38 (s, 1H), 4.61 (dd, J=9.17 and 3.75 Hz, 1H), 3.92–4.00 (m, 1H), 3.79–3.87 (m, 1H), 2.50–2.61 (m, 1H), 2.15–2.27 (m, 1H), 1.47 (s, 6H), 1.46 (s, 18H), 1.45 (s, 18H). HRMS (EI$^+$) m/z+Na: calc. 681.3623; found 681.3619.

Ex-10C

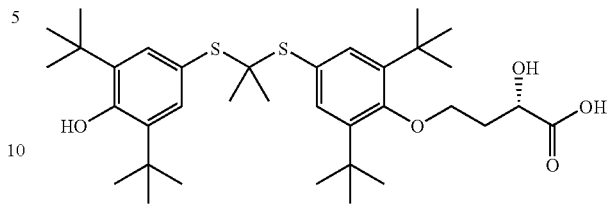

A 100 mL round bottom flask was charged with 3.7 g (5.6 mmol, 1 eq) of 2,6-di-tert-butyl-4-(1-{3,5-di-tert-butyl-4-[2-(2,2-dimethyl-[1,3]dioxolan-4(S)-yl)-ethoxy]-phenyl-sulfanyl}-1-methyl-ethylsulfanyl)-phenol (Ex-10B), 30 mL THF and 20 mL (20 mmol, 3.6 eq) 1 N NaOH. The reaction mixture was stirred at ambient temperature and monitored by TLC. Starting material was consumed after 1 hour and the reaction was quenched by addition of 50 mL of 1 N HCl. The product was extracted with EtOAc (3×100 mL). The combined organic extracts were washed with 50 mL of brine, dried over magnesium sulfate and concentrated under reduced pressure to yield a clear yellow oil. The oil was dissolved in 50 mL of hexanes and concentrated under reduced pressure three times. The residue was slurried in hexanes, filtered, washed with an additional 10 mL of hexanes and dried in vacuo to the yield 2.72 g (4.39 mmol, 79% yield) of 4-{2,6-di-tert-butyl-4-[1-(3,5-di-tert-butyl-4-hydroxy-phenylsulfanyl)-1-methyl-ethylsulfanyl]-phenoxy}-2(S)-hydroxy-butyric acid as a white solid, mp 113–114° C. $^1$H NMR (300 MHz, CDCl$_3$) δ: 7.57 (s, 2H), 7.47 (s, 2H), 5.39 (s, 1H), 4.52 (dd, J=8.48 and 3.31 Hz, 1H), 3.90–4.04 (m, 2H), 2.45–2.56 (m, 1H), 2.20–2.32 (m, 1H), 1.47 (s, 6H), 1.46 (s, 18H), 1.45 (s, 18H). Anal. calcd for C$_{35}$H$_{54}$O$_5$S$_2$: C67.92, H8.79, S10.36; found: C67.78, H8.84, S10.20. HRMS (EI$^+$) m/z+Na: calc. 641.3310; found 641.3309.

A 100 mL round bottom flask equipped with a nitrogen adapter and temperature probe was charged with 1.42 g (2.3 mmol, 1 eq) of 4-{2,6-di-tert-butyl-4-[1-(3,5-di-tert-butyl-4-hydroxy-phenylsulfanyl)-1-methyl-ethylsulfanyl]-phenoxy}-2(S)-hydroxy-butyric acid (Ex-10C), 25 mL THF and cooled to 0° C. The solution was treated with 6.9 mL (6.9 mmol, 3 eq) of 1.0 M borane in THF, warmed to 25° C. and monitored by HPLC. After stirring 6 hours at 25° C., the reaction was cooled using an ice bath, quenched with 15 mL of methanol and concentrated under reduced pressure. The residue was purified by silica gel chromatography (20% EtOAc/hexanes gradient to 80% EtOAc/hexanes) and dried in vacuo to yield 660 mg (1.1 mmol, 47% yield) of 4-{2,6-di-tert-butyl-4-[1-(3,5-di-tert-butyl-4-hydroxy-phenylsulfanyl)-1-methyl-ethylsulfanyl]-phenoxy}-butane-1,2(S)-diol as a white solid, mp 110–112° C. $^1$H NMR (300 MHz, CDCl$_3$) δ: 7.56 (s, 2H), 7.46 (s, 2H), 5.38 (s, 1H), 3.86–4.06 (m, 3H), 3.71–3.78 (m, 1H), 3.52–3.60 (m, 1H), 2.54 (d, 1H, J=4.08 Hz), 1.97–2.12 (m, 2H), 1.92 (t, 1H, J=6.19 Hz), 1.46 (s, 6H), 1.46 (s, 18H), 1.45 (s, 18H). Anal. calcd for C$_{35}$H$_{56}$O$_4$S$_2$: C69.49, H9.33, S10.60; found: C68.86, H9.25, S10.39 HRMS (EI$^+$) m/z+Na: calc. 627.3518; found 627.3539.

Example 11

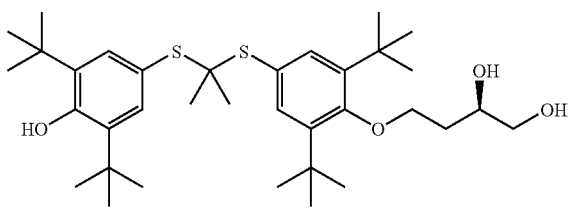

4-{2,6-Di-tert-butyl-4-[1-(3,5-di-tert-butyl-4-hydroxy-phenylsulfanyl)-1-methyl-ethylsulfanyl]-phenoxy}-butane-1,2(R)-diol 4-{2,6-Di-tert-butyl-4-[1-(3,5-di-tert-butyl-4-hydroxy-phenylsulfanyl)-1-methylethyl-sulfanyl]-phenoxy}-butane-1,2(R)-diol was prepared in the same manner as Ex-10 using (R)-(−)-2,2-dimethyl-5-oxo-1,3-dioxolane-4-acetic acid as a starting material and through intermediates Ex-11B and Ex-11C (shown below). $^1$H NMR (300 MHz, CDCl$_3$) δ: 7.56 (s, 2H), 7.46 (s, 2H), 5.38 (s, 1H), 3.86–4.06 (m, 2H), 3.71–3.78 (m, 1H), 3.52–3.60 (m, 1H), 2.54 (d, 1H, J=4.08 Hz), 1.97–2.12 (m, 2H), 1.92 (t, 1J=6.19 Hz), 1.46 (s, 6H), 1.46 (s, 18H), 1.45 (s, 18H). Anal. calcd for C$_{35}$H$_{56}$O$_4$S$_2$: C69.49, H9.33, S10.60; found: C69.33, H9.39, S10.54.

Ex-11B

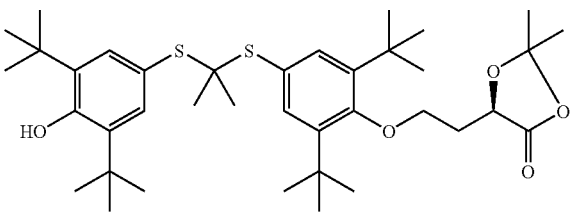

Ex-11C

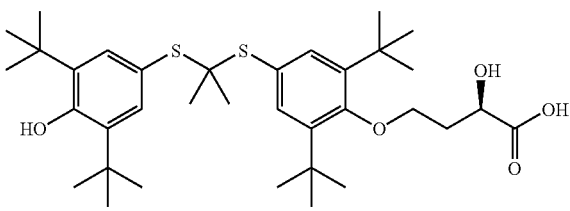

Example 12

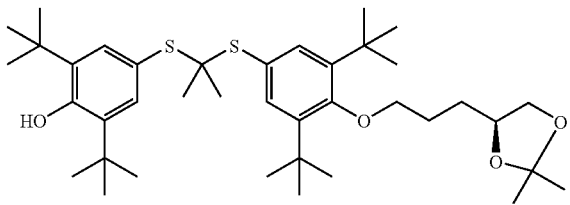

2,6-Di-tert-butyl-4-(1-{3,5-di-tert-butyl-4-[3-(2,2-dimethyl-[1,3]dioxolan-4(R)-yl)-propoxy]-phenylsulfanyl}-1-methyl-ethylsulfanyl)-phenol To a solution of probucol (2.93 g, 5.7 mmole) in 100 ml of THF were added Ph$_3$P (1.63 g, 6.2 mmole) and 3-[2,2-dimethyl-1,3-dioxolane-4(S)-yl]-propanol (1.0 g, 6.2 mmole). The mixture was cooled to 0° C. with an ice bath, and DEAD (1.1 g, 6.2 mmol) was then added dropwise under nitrogen. The mixture was stirred overnight while allowed to warm to room temperature and then heated to reflux. The reaction mixture was cooled and concentrated to an oily residue when HPLC and TLC showed that the new peak ceased to grow. Chromatography on silica gel with gradient solvent from hexanes to 25% EtOAc in hexanes to afford 1.3 g (35.1%) 2,6-di-tert-butyl-4-(1-{3,5-di-tert-butyl-4-[3-(2,2-dimethyl-[1,3]dioxolan-4(R)-yl)-propoxy]-phenylsulfanyl}-1-methyl-ethylsulfanyl)phenol as a white solid. $^1$H-NMR (CDCl$_3$) δ 7.53 (s, 2H), 7.45 (s, 2H), 5.37(s, 1H), 4.05–4.17 (m, 2H), 3.71–3.77 (m, 2H), 3.35 (t, J=2.5 Hz, 1H), 1.90–2.00 (m, 2H), 1.63–1.73 (m, 2H), 1.42–1.46 (m, 42H). MS m/z: 676.4429 ([M+NH$_4$]$^+$, 25%)

Example 13

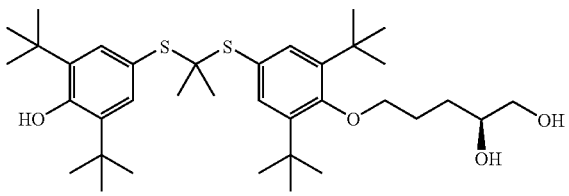

5-{2,6-Di-tert-butyl-4-[1-(3,5-di-tert-butyl-4-hydroxy-phenylsulfanyl)-1-methyl-ethylsulfanyl]-phenoxy}-pentane-1,2(S)-diol To a solution of 2,6-di-tert-butyl-4-(1-{3,5-di-tert-butyl-4-[3-(2,2-dimethyl-[1,3]dioxo-lan-4(R)-yl)-propoxy]-phenylsulfanyl}-1-methyl-ethylsulfanyl)-phenol (Ex-11, 230 mg, 0.35 mmol) in 20 ml MeOH, was added 1.0 N HCl dropwise until the mixture turned cloudy. Then small amount of MeOH was added to the mixture until it became clear. The mixture was stirred at room temperature, and HPLC indicated that the reaction completed within 2 hours. The mixture was neutralized with 5N KOH and extracted with EtOAc. The combined organic phase was washed with water, dried over MgSO$_4$, and concentrated to dryness. The residue was purified by silica gel column chromatography to give 0.2 g (93%) 5-{2,6-di-tert-butyl-4-[1-(3,5-di-tert-butyl-4-hydroxy-phenylsulfanyl)-1-methyl-ethylsulfanyl]-phenoxy}-pentane-1,2(S)-diol as a white solid, mp 68–71° C. $^1$H-NMR (CDCl$_3$) δ 7.53 (s, 2H), 7.45 (s, 2H), 5.36(s, 1H), 3.67–3.79 (m, 4H), 3.46–3.52 (m, 1H), 1.91–2.17 (m, 4H), 1.42–1.45 (m, 42H). MS m/z: 636.4119 ([M+NH$_4$]$^+$, 20%). Anal. calcd for C$_{36}$H$_{58}$O$_4$S$_2$: C, 69.86; H, 9.44; S, 10.36; found: C, 70.10; H, 9.15; S, 10.13.

Example 14

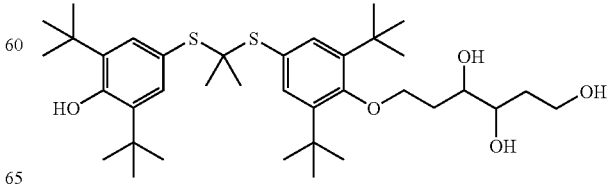

6-{2,6-Di-tert-butyl-4-[1-(3,5-di-tert-butyl-4-hydroxy-phenylsulfanyl)-1-methyl-ethylsulfanyl]-phenoxy}-hexane-1,3,4-triol

Ex-14A

To a solution of 4-methylmorpholine (8.1 g, 70 mmol) in acetone:water (7:1, 170 mL) at 0° C. was added a solution of osmium tetraoxide in tert-butanol (2.5 wt %, 7.1 mL, 0.70 mmol) followed by hex-3-enedioic acid dimethyl ester(10.0 g, 58 mmol) in acetone (50 mL). The reaction was stirred at 0° C. for 15 min and allowed to warm to rt and stirred for an additional 18 h. The mixture was quenched with sodium hydrogensulfite (5 g) and stirred vigorously for 30 min. The resulting red slurry was filtered through a pad of Celite and rinsed with several portions of fresh acetone, the filtrate was then acidified with 3 N HCl and concentrated to approx. 25% volume. The residue was diluted with ethyl acetate (75 mL) and the layers were separated and further extracted with ethyl acetate (10×75 mL), the organic extracts were dried over sodium sulfate, and concentrated under reduced pressure to an off white solid, mp 80–81° C. Recrystallization (ethyl acetate/hexanes) afforded 10.1 g (84%) of 3,4-dihydroxy-hexanedioic acid dimethyl ester as a white solid. $^1$H-NMR (300 MHz, CDCl$_3$) δ3.97–3.99 (m, 2H), 3.72 (s, 6H), 3.14 (brs, 2H), 2.54–2.72 (m, 4H). HRMS (EI) calcd for C$_8$H$_{14}$O$_6$ (M+H), 207.0869; found, 2070864. Anal. calcd. for C$_8$H$_{14}$O$_6$: C, 46.60; H, 6.84; found: C, 46.64; H, 6.85.

Ex-14B

To a solution of 3,4-dihydroxy-hexanedioic acid dimethyl ester (Ex-14A, 8.8 g, 43 mmol) in toluene (65 mL) was added triethyl orthoformate (12.6 g, 85.4 mmol) and the mixture was heated at reflux with a Dean-Stark trap for 24 h. The reaction mixture was then distilled to remove toluene and excess triethyl orthoformate and dried in vacuo to give (2-ethoxy-5-methoxycarbonylmethyl-[1,3]dioxolan-4-yl)-acetic acid methyl ester as a colorless oil (11.0 g, 99%). This material used without further purification. $^1$H-NMR (300 MHz, CDCl$_3$) δ5.80 (s, 1H),4.41 (q, 1H, J=6.3 Hz), 4.28 (q, 1H, J=6.3 Hz), 3.71 (s, 6H), 3.78 (q, 2H, J=7.2 Hz), 2.83 (dd, 1H, J=9.3, 6.7 Hz), 2.70 (dd, 1H, J=6.7, 3.0 Hz), 1.22 (t, 3H, J=7.2 Hz). HRMS (EI) calcd for C$_{11}$H$_{18}$O$_7$ (M–H), 261.0974; found, 261.0970.

Ex-14C

To a solution of (2-ethoxy-5-methoxycarbonylmethyl-[1,3]dioxolan-4-yl)-acetic acid methyl ester (Ex-14B, 11.0 g, 42 mmol) in tetrahydrofuran (75 mL) at 0° C. was added a solution of LAH in tetrahydrofuran (1 M, 63 mL, 63 mmol) dropwise over a 1 h period. The reaction mixture was allowed to warm to rt and stir for 2 h at which time the solution was then cooled back down to 0° C. and carefully quenched with sodium sulfate decahydrate. The mixture was concentrated under reduced pressure and the residue was diluted with equal portions of a saturated Rochelle salt solution and ethyl acetate (approx. 150 mL each) and the slurry was vigorously stirred overnight. The layers were then separated and the aqueous layer was extracted with ethyl acetate (4×100 mL), the organic extracts dried over sodium sulfate, filtered and concentrated under reduced pressure. Drying in vacuo gave 2-[2-ethoxy-5-(2-hydroxy-ethyl)-[1,3]dioxolan-4-yl]-ethanol (7.6 g, 88%) as a colored oil. This material was used without further purification. $^1$H-NMR (300 MHz, CDCl$_3$) δ5.82(s, 1H), 4.11–4.17 (m, 1H,), 3.92–3.97 (m, 1H), 3.80–3.86 (m, 4H), 3.61 (q, 2H, J=7.0 Hz), 2.30 (brs, 1H), 2.22 (brs, 1H), 1.76–1.94 (m, 4H), 1.23 (t, 3H, J=7.0 Hz).

Ex-14D

To a solution of probucol (19.0 g, 37 mmol) and 2-[2-ethoxy-5-(2-hydroxy-ethyl)-[1,3]dioxolan-4-yl]-ethanol (Ex-14C, 7.6 g, 37 mmol) in tetrahydrofuran (160 mL) was added triphenylphosphine (10.6 g, 41 mmol) and the resulting mixture was cooled to 0° C. Diethyl azodicarboxylate (7.1 g, 41 mmol) was then added dropwise, stirred at 0° C. for 30 min, and allowed to warm to rt. The solution was ultimately heated to 65° C. and stirred for an additional 18 h for the reaction to complete. The reaction mixture was concentrated under reduced pressure to an orange viscous oil and titurated with hexanes and the resulting slurry was stirred at rt for 30 min. The solution was filtered to remove the triphenylphosphine oxide and the filtrate was concentrated under reduced pressure. The residue was subjected to silica gel chromatography (10% ethyl acetate/hexanes with a gradual increase to 30% ethyl acetate/hexanes) to afford 7.4 g (30%) of 2,6-di-tert-butyl-4-[1-(3,5-di-tert-butyl-4-{2-[2-ethoxy-5-(2-hydroxy-ethyl)-[1,3]dioxolan-4-yl]-ethoxy}-phenylsulfanyl)-1-methyl-ethylsulfanyl]-phenol as a white solid. $^1$H-NMR (300 MHz, CDCl$_3$) δ7.53 (s, 2H), 7.45 (s, 2H), 5.81 (s. 1H), 5.36 (s, 1H), 4.09–4.19 (m, 2H), 3.84–3.92 (m, 4H), 3.59 (q, 2H, J=6.8 Hz), 2.17–2.19 (m, 2H), 2.02–2.05 (m, 1H), 1.86–1.96 (m, 2H), 1.42–1.44 (m, 42H), 1.19–1.24 (m, 3H). HRMS (ESI) calcd for C$_{40}$H$_{64}$O$_6$S$_2$ (M+K), 727.4042; found, 727.4050. Anal. calcd. for C$_{40}$H$_{64}$O$_6$S$_2$: C, 66.62, H, 9.55, S, 8.68; found: C, 66.65, H, 9.35, S, 9.01.

2,6-Di-tert-butyl-4-[1-(3,5-di-tert-butyl-4-{2-[2-ethoxy-5-(2-hydroxy-ethyl)-[1,3]dioxo-lan-4-yl]-ethoxy}-phenylsulfanyl)-1-methyl-ethylsulfanyl]-phenol (Ex-13D, 4.0 g, 5.7 mmol) was dissolved in methanol (60 mL). Acetic acid (2.8 mL) and water (2.8 mL) were added and the resultant mixture was stirred at reflux for 3 h. The reaction mixture was concentrated under reduced pressure and the residue was diluted with water (100 mL) and extracted with dichloromethane (3×100 mL). The combined organic extracts were dried over sodium sulfate and concentrated to an off-white foam. The residue was dissolved in methanol (60 mL) and potassium carbonate (1.6 g) was added. The mixture was stirred at room temperature for 1.5 h and concentrated under reduced pressure and the residue was diluted with water (100 mL). The solution was extracted with dichloromethane (3×100 mL), dried over sodium sulfate, and concentrated to a white foam. Following silica gel chromatography (2:1 ethyl acetate:hexanes) gave 2.2 g (65%) of 6-{2,6-di-tert-butyl-4-[1-(3,5-di-tert-butyl-4-hydroxy-phenylsulfanyl)-1-methyl-ethylsulfanyl]-phenoxy}-hexane-1,3,4-triol as a white solid, mp 75–77° C. $^1$H-NMR (300 MHz, CDCl$_3$) δ7.54 (s, 2H), 7.45 (s, 2H), 5.36 (s, 1H), 3.92–3.99 (m, 4H), 3.78 (brs, 2H), 2.99 (d, 1H, J=3.8 Hz), 2.78 (d, 1H, J=3.8 Hz), 2.15 (t, 1H, J=4.6 Hz), 2.02–2.11 (m, 2H), 1.83–1.85 (m, 2H), 1.43–1.44 (m, 42H). HRMS (ESI) calcd for C$_{37}$H$_{60}$O$_5$S$_2$ (M+Na), 671.3780; found, 671.3775. Anal. calcd. for C$_{37}$H$_{60}$O$_5$S$_2$: C, 68.47, H, 9.32, S, 9.88; Found: C, 68.62, H, 9.49, S, 9.59.

Example 15

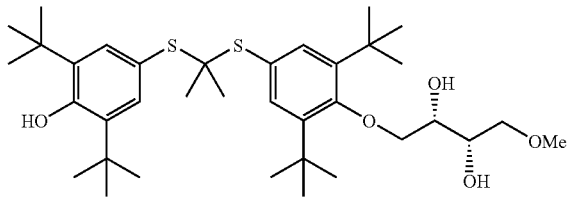

1-{2,6-Di-tert-butyl-4-[1-(3,5-di-tert-butyl-4-hydroxyphenylsulfanyl)-1-methylethyl sulfanyl]phenoxy}-4-methoxybutane-2(S),3(S)-diol

Ex-15A

To a solution of the diastereomers A & B obtained from Ex-1A (0.40 g, 0.59 mmol) in tetrahydrofuran (5 mL) at rt was added sodium hydride (60% dispersion in mineral oil, 0.052 g, 2.2 mmol) and the resulting mixture was stirred at rt for 30 min. Methyl iodide (0.083 g, 0.59 mmol) was then added drop wise and allowed to stir at rt for 18 h. Upon completion, the reaction was diluted with water (10 mL) and extracted with ethyl acetate (3×15 mL). The combined organic extracts were washed with brine (2×30 mL), dried over sodium sulfate and concentrated to an orange foam. Silica gel chromatography (9:1 ethyl acetate/hexanes) afforded 0.24 g (60%) of 2,6-di-tert-butyl-4-{1-[3,5-di-tert-butyl-4-(2-ethoxy-5(S)-methoxymethyl-[1,3]dioxolan-4(S)-ylmethoxy)-phenylsulfanyl]-1-methyl-ethylsulfanyl}-phenol (mixture of two diastereomers) as an off white foam, mp 65–68° C. $^1$H-NMR (300 MHz, CDCl$_3$) δ7.54 (s, 2H), 7.44 (s, 2H), 5.90 (s, 1H), 5.36 (s, 1H), 4.53–4.56 (m, 1H), 3.86–4.04 (m, 3H), 3.55–3.73 (m, 4H), 3.40 (s, 3H), 1.43–1.45 (m, 42H), 1.26 (t, 3H, J=7.2 Hz). HRMS (ESI) calcd for C$_{39}$H$_{62}$O$_6$S$_2$ (M+K), 729.3625; found, 729.3610.

2,6-Di-tert-butyl-4-{1-[3,5-di-tert-butyl-4-(2-ethoxy-5(s)-methoxymethyl-[1,3]dioxolan-4(S)-ylmethoxy)-phenylsulfanyl]-1-methyl-ethylsulfanyl}-phenol (Ex-15A, 0.72 g, 1.1 mmol) was dissolved in methanol (3 mL). Acetic acid (0.14 mL) and water (0.14 mL) were added and the resultant mixture was stirred at reflux for 3 h. The reaction mixture was diluted with water (10 mL) and extracted with dichloromethane (3×10 mL). The combined organic extracts were dried over sodium sulfate and concentrated to an off-white foam. The residue was dissolved in methanol (3 mL) and potassium carbonate (0.085 g) was added. The mixture was stirred at room temperature for 30 min and diluted with water (10 mL). The solution was extracted with dichloromethane (3×10 mL), dried over sodium sulfate, and concentrated to a white foam. Silica gel chromatography (3:1 ethyl acetate: hexanes) gave 0.18 g (99%) of 1-{2,6-di-tert-butyl-4-[1-(3,5-di-tert-butyl-4-hydroxyphenylsulfanyl)-1-methylethylsulfanyl]phenoxy}-4-methoxybutane-2(S),3(S)-diol as a white solid, mp 62–64° C. $^1$H-NMR (CDCl$_3$) δ 7.55 (s, 2H), 7.45 (s, 2H), 5.36 (s, 1H), 4.25–4.26 (m, 1H), 3.86–3.90 (m, 3H), 3.59–3.60 (m, 2H), 3.41 (s, 3H), 2.79 (d, 1H, J=4.8 Hz), 2.63 (d, 1H, J=4.8 Hz), 1.42–1.45 (m, 42H). HRMS (ESI) calcd for C$_{36}$H$_{58}$O$_5$S$_2$ (M+Na), 657.3624; Found, 657.3630. Anal. calcd. for C$_{36}$H$_{58}$O$_5$S$_2$: C, 68.10, H, 9.21, S, 10.10; Found: C, 68.47, H, 9.38, S, 9.85.

Example 16

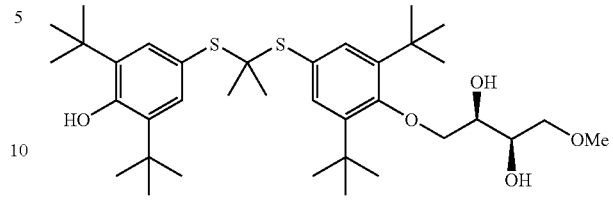

1-{2,6-Di-tert-butyl-4-[1-(3,5-di-tert-butyl-4-hydroxyphenylsulfanyl)-1-methylethyl sulfanyl]phenoxy}-4-methoxybutane-2(R),3(R)-diol The title compound was prepared using the same procedure as described for Ex-14 from the diastereomers obtained from Ex-2 as a white solid (4.9 g, 97%), mp 68–70 ° C. $^1$H-NMR (CDCl$_3$) δ 7.55 (s, 2H), 7.45 (s, 2H), 5.36 (s, 1H), 4.25–4.27 (m, 1H), 3.86–3.94 (m, 3H), 3.59–3.61 (m, 2H), 3.41 (s, 3H), 2.80 (d, 1H, J=4.8 Hz), 2.64 (d, 1H, J=4.8 Hz), 1.44–1.45 (m, 42H). HRMS (ES1) calcd for C$_{36}$H$_{58}$O$_5$S2 (M+Na), 657.3624; Found, 657.3628. Anal. calcd. for C$_{36}$H$_{58}$O$_5$S$_2$: C, 68.10, H, 9.21, S, 10.10; Found: C, 68.64, H, 9.41, S, 9.93.

Example 17

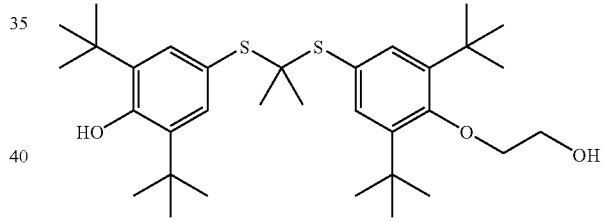

2,6-Di-tert-butyl-4-{1-[3,5-di-tert-butyl-4-(2-hydroxy-ethoxy)-phenylsulfanyl]-1-methyl-ethylsulfanyl}-phenol A 100 mL, 2-neck round bottom flask equipped with a nitrogen adapter and a temperature probe was charged with 5.0 g (8.7 mmol, 1 eq) of {2,6-Di-tert-butyl-4-[1-(3,5-di-tert-butyl-4-hydroxy-phenylsulfanyl)-1-methyl-ethylsulfanyl]-phenoxy}-acetic acid and 40 mL of anhydrous THF. The solution was cooled to 0° C. using an ice bath and 26.1 mL of 1.0 M (26.1 mmol, 3 eq) borane in THF at a rate such that the maximum temperature was less than 30° C. The solution was warmed to 30° C. and consumption of starting material was monitored by TLC. After 4 hours, the flask was cooled to 0° C. using an ice bath and 75 mL of methanol was slowly added. The resulting solution was concentrated under reduced pressure. The resulting oil was dissolved in 50 mL of methanol and concentrated under reduced pressure two more times. The residue was slurried in 50 mL of hexanes and concentrated under reduced pressure a total of 4 times. The residue was taken up in 50 mL of hexanes and the product was allowed to slowly precipitate. The precipitate was collected by vacuum filtration, washed with 10 mL of hexanes and dried in vacuo to yield 3.1 g (5.6 mmol, 64% yield) of the title compound as a white powder, mp 146–147° C.; $^1$H NMR (300 MHz, CDCl$_3$) d 7.56 (s, 2H), 7.45 (s, 2H), 5.37 (s, 1H), 4.03 (t, J=5.2 Hz, 2H), 2H), 3.92 (t, J=5.1 Hz, 2H), 1.47 (s, 6H), 1.46 (s, 18H), 1.45 (s, 18H). Anal. calcd for C$_{33}$H$_{52}$O$_3$S$_2$: C70.66, H9.34, S11.43; found: C70.36, H9.37, S11.35. HRMS (EI$^+$), m/z: calc. 560.3358; Found 560.3347

Example 18

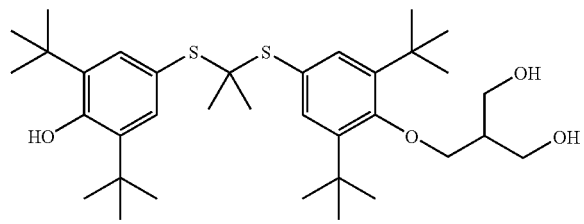

2-{2,6-Di-tert-butyl-4-[1-(3,5-di-tert-butyl-4-hydroxyphenylsulfanyl)-1-methylethyl-sulfanyl] phenoxymethyl}propane-1,3-diol To a solution of probucol (1.0 g, 1.9 mmol) and 3-(tert-butyldimethylsilanyloxy)-2-(tert-butyldimethylsilanyloxymethyl)propan-1-ol (1.3 g, 3.9 mmol; Kim, H. S. et al. J. Med. Chem. 2001, 44, 3092) in tetrahydrofuran (20 mL) was added triphenylphosphine (1.0 g, 3.9 mmol) and the resulting mixture was cooled to 0° C. Diethyl azodicarboxylate (0.60 g, 3.9 mmol) was then added drop wise, stirred at 0° C. for 30 min, and allowed to warm to rt. The solution was ultimately warmed to 50° C. and stirred for an additional 18 h for the reaction to complete. The reaction mixture was concentrated under reduced pressure to a brown oil and subjected to silica gel chromatography (100% hexanes then 1–5% CH$_2$Cl$_2$/hexanes) to afford 0.33 g (20%) of the expected ether as a yellow foam (mixed with trace amts of probucol starting material). R$_f$ 0.61 (10% ethyl acetate/hexanes). $^1$H-NMR (300 MHz, CDCl$_3$) δ7.53 (s, 2H), 7.45 (s, 2H), 5.35 (s, 1H), 3.76–3.81 (m, 6H), 2.34–2.38 (m, 1H), 1.4–1.44 (m, 42H), 0.88 (s, 18H), 0.039 (s, 12H). LRMS (ESI) m/z (%) 855 (M+Na, 90), 595.5 (100). This material was carried forward without any further purification. To a solution containing this material (0.10 g, 0.12 mmol) in tetrahydrofuran (10 mL) was added tetrabutylammonium fluoride (1 M in tetrahydrofuran, 0.40 mL, 0.40 mmol) and the reaction was stirred at rt for 2 h. The solution was ultimately warmed to 35° C. and stirred for an additional 2 h for the reaction to complete. The reaction mixture was diluted with a 50% aqueous solution of ammonium chloride (20 mL) and extracted with methylene chloride (3×20 mL). The combined organic layers were washed with water (2×10 mL), brine (1×10 mL), dried over sodium sulfate and the solvent was removed under reduced pressure. The crude residue was purified by silica gel chromatography (1:1 ethyl acetate/hexanes) to give 0.032 g (45%) 2-{2,6-di-tert-butyl-4-[1-(3,5-di-tert-butyl-4-hydroxyphenylsulfanyl)-1-methylethyl-sulfanyl]phenoxymethyl}propane-1,3-diol as a pale yellow foam. R$_f$ 0.34 (50% ethyl acetate/hexanes). $^1$H-NMR (300 MHz, CDCl$_3$) δ7.55 (s, 2H), 7.44 (s, 2H), 5.36 (s, 1H), 3.83–4.02 (m, 6H), 2.50–2.56 (m, 1H), 2.03–2.07 (m, 2H); 1.42–1.44 (m, 42H). LRMS (EI) m/z (%) 604 (M$^+$, 0.1), 279 (100). HRMS (ESI) calcd for C$_{35}$H$_{56}$O$_4$S$_2$ (M+K), 643.3257; Found, 643.3255. Anal. calcd for C$_{35}$H$_{56}$O$_4$S$_2$: C, 69.49; H, 9.33; S, 10.60; Found: C, 69.28; H, 9.09; S, 10.33.

Example 19

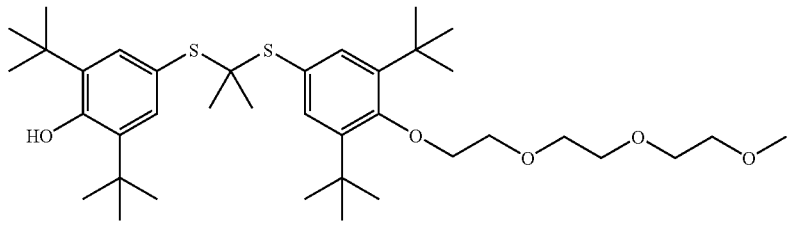

2,6-Di-tert-butyl-4-[1-(3,5-di-tert-butyl-4-{2-[2-(2-methoxyethoxy)-ethoxy]ethoxy}-phenyl-sulfanyl)-1-methylethylsulfanyl]phenol To a solution of probucol (2.0 g, 3.9 mmol) and tri (ethylene glycol) monomethyl ether (1.27 g, 7.7 mmol) in tetrahydrofuran (40 mL) was added triphenylphosphine (2.0 g, 7.7 mmol), and the resulting mixture was cooled to 0° C. Diethyl azodicarboxylate (1.3 g, 7.7 mmol) was then added dropwise, stirred at 0° C. for 30 min, and allowed to warm to rt. The solution was ultimately warmed to 40° C. and stirred for an additional 2 h for the reaction to go to completion. The reaction mixture was concentrated under reduced pressure to a brown oil. Silica gel chromatography (10–30% ethyl acetate/hexanes) afforded 0.96 g (40%) of the expected polyether as a viscous yellow oil. R$_f$ 0.25 (30% ethyl acetate/hexanes). $^1$H-NMR (300 MHz, CDCl$_3$) δ7.53 (s, 2H, Ph-H), 7.45 (s, 2H, Ph-H), 5.36 (s, 1H, Ph-OH), 3.89 (brs, 4H, Ph-OCH$_2$CH$_2$O), 3.67–3.75 (m, 6H, OCH$_2$CH$_2$OCH$_2$), 3.56–3.58 (m, 2H, OCH$_2$), 3.39 (s, 3H, OCH$_3$), 1.42–1.44 (m, 42H, tert-butyls and S,S'-isopropylidene). LRMS (ESI) m/z (%) 685 (M+Na, 100). HRMS (ESI) calcd for C$_{38}$H$_{62}$O$_5$S$_2$ (M+K): 701.3676; Found, 701.3649. Anal. calcd for C$_{38}$H$_{62}$O$_5$S$_2$: C, 68.84; H, 9.43; S, 9.67. Found: C, 68.21; H, 9.20; S, 9.91.

Example 20

Testing Biological Activity of Compounds

The ability of a compound described herein to inhibit the expression of VCAM-1 or in the treatment of diseases in a host can be assessed using any known method, including those described in detail below.

In Vitro VCAM-1 Assay—Method 1

Cell Culture and compound dosing: Cultured primary human aortic (HAEC) or pulmonary (HPAEC) endothelial cells were obtained from Clonetics, Inc., and were used below passage 9. Cells were seeded in 96 well plates such that they would reach 90–95% confluency by the following day. On the following day the cells were stimulated with TNF-α (1 ng/ml) in the presence or absence of compounds dissolved in DMSO such that the final concentration of DMSO is 0.25% or less. To establish a dose curve for each compound, four concentrations in 2- to 5-fold increments were used. Cells were exposed to TNF-α and compounds for approximately 16 hours. The next day the cells were examined under microscope to score for visual signs of toxicity or cell stress.

Following 16 hr exposure to TNF-α and compound the media was discarded and the cells were washed once with Hanks Balanced Salt Solution (HBSS)/Phosphate buffered saline (PBS) (1:1). Primary antibodies against VCAM-1 (0.25 μg/ml in HBSS/PBS+5% FBS) were added and incubated for 30–60 minutes at 37° C. Cells were washed with HBSS/PBS three times, and secondary antibody Horse Radish Peroxidase (HRP)-conjugated goat anti-mouse IgG (1:500 in HBSS/PBS+5% FBS) were added and incubated for 30 minutes at 37° C. Cells were washed with HBSS/PBS four time and TMB substrate were added and incubated at room temperature in the dark until there was adequate development of blue color. The length of time of incubation was typically 5–15 minutes. 2N sulfuric acid was added to stop the color development and the data was collected by reading the absorbance on a BioRad ELISA plate reader at OD 450 nm. The results are expressed as $IC_{50}$ values (the concentration (micromolar) of compound required to inhibit 50% of the maximal response of the control sample stimulated by TNF-α only). $IC_{50}$'s of tested compounds are tabulated in Biological Table 1.

In Vitro VCAM-1 Assay—Method 2

Cultured primary human aortic (HAEC) or pulmonary artery (HPAEC) endothelial cells are obtained from Bio-Whittaker (formerly Clonetics), and are used below passage 9. Cells are seeded in 96-well plates such that they will reach ~95% confluency by the following day (i.e.10,000 cells/well). Compounds are reconstituted in DMSO (100%) and sonicated to ensure maximum dissolution. Dilutions are then made in DMSO to 500× of final concentrations. These stocks are then diluted 500× into cell culture media (EGM-2 Mv, BioWhittaker) and placed overnight in tissue culture incubator (37° C., 5% CO2) to allow maximum dissolution).

Media is removed from the cells and replaced with the prewarmed dosing media. Cells are predosed in this manner for 19 hours at 37° C., 5% CO2. Remove media again from the cells and replace with prepared dosing media containing TNFα (1.5 ng/ml). Allow stimulation to continue for 4 hours at 37° C., 5% $CO_2$. Media is removed and saved for evaluation of secreted factors as needed. Cells are used for quantitating surface VCAM-1, followed by Hoescht nuclear stain for cell number to determine toxicity. Assay for surface VCAM-1 continues as described in Method 1. IC50's of tested compounds are tabulated in Biological Table 1.

Biological Table 1

| Compound | VCAM-1 $IC_{50}$ (μM)[a] | |
|---|---|---|
| | Method 1 | Method 2 |
| Ex-1 | 7 | 9 |
| Ex-2 | 5 | NT |
| Ex-3 | 6 | NT |
| Ex-4 | 7 | NT |
| Ex-5 | 6 | NT |
| Ex-6 | 6 | NT |
| Ex-10 | 40 | 8 |
| Ex-11 | >50 | 7 |
| Ex-13 | NT | 11 |
| Ex-14 | 21 | 9.2 |
| Ex-18 | 13 | 6 |
| Ex-19 | >50 | NT |

[a]NT = not tested.

Cytokine Screening

Cytokines are extracellular signaling proteins produced by many cell types playing a central role in human immune response, and can be categorized as either pro-inflammatory or anti-inflammatory in action. TNF-α, IL-1β and IL-6 are major pro-inflammatory cytokines implicated in the pathogenesis of numerous diseases. The expression of these proinflammatory cytokines is also redox-regulated (Haddad, J. J.; Saade, N. E.; Safieh-Garabedian, B. Redox regulation of TNF-α Biosynthesis: Augmentation by Irreversible Inhibition of γ-Glutamylcysteine Synthetase and the Involvement of an IκB-α/NF-κB-independent Pathway in Alveolar Epithelial Cells. *Cell Signal.* 2002, 14, 211–218).

Fresh cryopreserved hPBMCs (1 million cells/ml; Clonetics, Inc.) were pretreated with test compound for 1 hr in lymphocyte growth media-3 (Clonetics, Inc.), followed by stimulation with 1 μg/ml of LPS for another 2 hr in the presence of test compound. Conditioned media was collected and assayed for secreted TNF-α, IL-1β and IL-1β using commercially available human ELISA kits (R&D Systems). Samples were measured in duplicate and data presented as mean ± standard deviation. Each experiment was repeated at least three times with similar results. Biological Table 2 shows the results of testing with Examples 1 and 2. Biological Table 3 is an inhibitory profile of selected compounds on LPS-induced secretion of cytokines from hPBMN cells, where all $IC_{50}$ numbers reflect an average of at least three determinations.

Biological Table 2

| Compd | TNF-α ($IC_{50}$, μM) | IL-1β ($IC_{50}$, μM) | IL-6 ($IC_{50}$, μM) |
|---|---|---|---|
| Ex-1 | 4.0 ± 1.0 | 7.7 ± 0.6 | 1.7 ± 0.9 |
| Ex-2 | 3.3 ± 0.3 | 8.0 ± 0.0 | 1.2 ± 0.3 |

Biological Table 3

| Compound | TNF-α ($IC_{50}$, μM) | IL-1β ($IC_{50}$, μM) | IL-6 ($IC_{50}$, μM) |
|---|---|---|---|
| Ex-1 | 5.1 | 7.7 | 1.7 |
| Ex-2 | 1.6 | 8.0 | 1.2 |
| Ex-10 | 3.8 | NT | NT |

-continued

Biological Table 3

| Compound | TNF-α (IC$_{50}$, μM) | IL-1β (IC$_{50}$, μM) | IL-6 (IC$_{50}$, μM) |
|---|---|---|---|
| Ex-11 | 4.4 | NT | NT |
| Ex-18 | 4.5 | NT | NT |

[a]NT = not tested.

DTH Model of Inflammation in Mice.

The methylated bovine serum albumin (mBSA)-induced delayed-type hypersensitivity (DTH) model of mice is generally used for screening compounds with anti-inflammatory effects (Sarnstrand et al., Pharmacol. Exp. Ther. 1999, 288, 1174–84). Compounds of Ex-1 and Ex-2 were tested in this model, dosed subcutaneously at 24 and 2 hrs prior to challenge at doses of 50 and 25 mg/kg with cyclosporin A (CSA) as positive control.

Male BALB/c mice (20–25 g) were sensitized on day 0 by intradermal abdominal injection of 100 μL of a 1:1 emulsion of mBSA (5 mg/ml) and Freund's complete adjuvant. On day 7, the mice were challenged by injecting 25 μL of mBSA (5 mg/ml) into the footpad of the right hindpaw and the left hindpaw was injected with saline. Mice were treated by s.c. injection of test compound 24 hrs and 2 hrs before the challenge. Twenty four hours after challenge mice were sacrificed by CO$_2$ inhalation. The feet were removed by cutting just above the heel with scissors, and the mass of the saline-injected foot was subtracted from the mass of the mBSA injected foot to determine the amount of swelling that occurred in the latter. Inhibition of swelling for test compound group was calculated, taking the swelling of the vehicle-treated group as 100%. The results from the DTH model are summarized for examples 1 and 2 in Biological Table 4 using cyclosporine A (CSA) as a positive control.

Biological Table 4

| Compound Number | Percent Inhibition |
|---|---|
| Ex. 1, 50 mg/Kg | +65 |
| Ex. 2, 50 mg/Kg | +60 |
| Ex. 1, 25 mg/Kg | +40 |
| Ex. 2, 25 mg/Kg | +25 |
| CSA (control) 25 mg/KG | +20 |

In Vivo Screening Protocol: Asthma Model

Balb/C mice (6–8 weeks old) were sensitized to ovalbumin (ova) (8 ug ova absorbed in 3.3 mg Alum inject) on days 0 and 5. On day 12, the mice were aerosol challenged with 0.5% ovalbumin dissolved in sterile saline for 1 hr in the AM, and then again in the PM (at least 4 hr apart). On day 14, the mice were anesthetized with ketamine/xylazine/acepromazine cocktail, exsanguinated, and then euthanized. Following blood collection, bronchoaveolar lavage (BAL) was performed on each animal. Total cell counts were conducted on the lavage fluid, which was subsequently diluted with cell media 1:1. Slides of the lavage fluid were made by spinning the samples with a cytospin centrifuge and then air drying. Cell differentials of the lavage fluid were determined by microscopic evaluation of hematoxylin and eosin-stained slides. Data are expressed as the % inhibition of eosinophilia in the BAL fluid compared to the vehicle control. Compounds were administered except where noted by subcutaneous injection once daily from day 11–13. The formulations used contained various mixtures of the following excipients (propylene glycol, polyethylene glycol, Tween 80, Glycofurol). The results from the asthma model are in Biological Table 5.

In Vivo Screening Protocol: Rheumatoid Arthritis Model

Female Lewis rats (200–250 g) were sensitized with Freund's complete adjuvant (100 ug) by subcutaneous injection at the base of the tail. Paw swelling was monitored by measuring the volume of each foot with a plethysmometer on days 5, 8, 12–15. Animals were euthanized on day 15. Animals were dosed subcutaneously, once daily from days 7–14. Data is expressed as the % inhibition of paw swelling (AUC of the paw volume vs time curve d5–15) compared with vehicle control. The formulations used contained various mixtures of the following excipients (propylene glycol, polyethylene glycol, Tween 80, Glycofurol). The results from the rheumatoid arthritis model are shown in Biological Table 5.

Biological Table 5

In vivo efficacy[a]

| Compound | Rheumatoid arthritis model (25 mg/kg, sc, qd, d 11–14, inhibition of BALF eosinophilia in percentage) | Asthma model (25 mg/kg, sc, qd, d 7–13, inhibition of paw swelling in percentage) |
|---|---|---|
| Ex-1 | 87 | NT |
| Ex-2 | 65 | 75 |
| Ex-10 | 78 | 85 |
| Ex-11 | 95 | 85 |
| Ex-13 | 60 | NT |
| Ex-14 | 84 | NT |
| Ex-16 | 44 | 63 |
| Ex-18 | 60 | 83 |

[a]NT = not tested.

What is claimed is:

1. A compound of Formula II

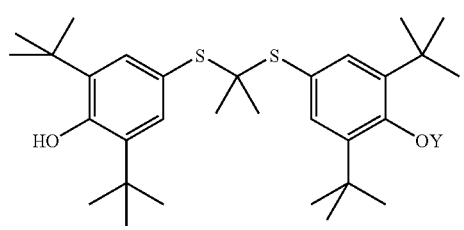

II or a pharmaceutically acceptable salt or ester thereof, wherein:

Y is selected from the group consisting of:

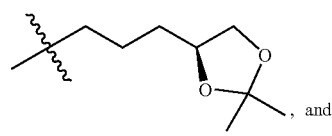

, and

-continued

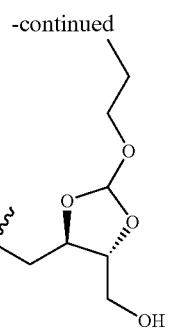

or a compound selected from the group consisting of

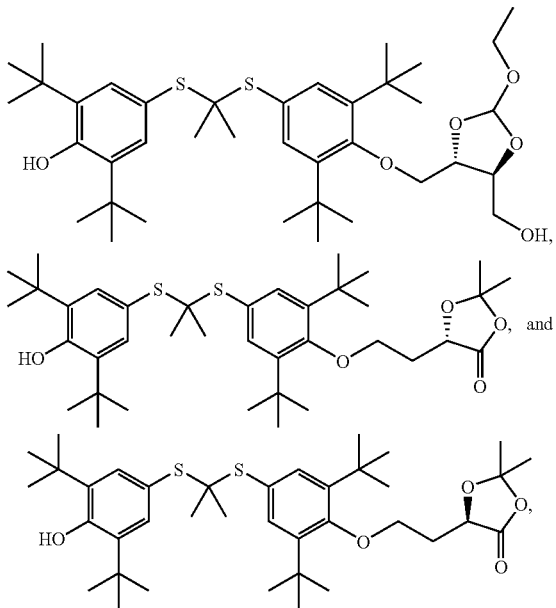

or a pharmaceutically acceptable salt or ester thereof.

2. The compound of claim 1 wherein the compound is a compound of Formula II wherein Y is

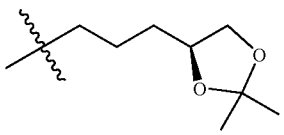

or a pharmaceutically acceptable salt or ester thereof.

3. A pharmaceutical composition comprising a therapeutically effective amount of a compound of claim 1 and a pharmaceutically acceptable carrier.

4. A method for the treatment of an inflammatory disorder, comprising administering an effective amount of a compound of claim 1.

5. The method of claim 4, wherein the disorder is arthritis.

6. The method of claim 4, wherein the disorder is rheumatoid arthritis.

7. The method of claim 4, wherein the disorder is asthma.

8. The method of claim 4, wherein the disorder is allergic rhinitis.

9. The method of claim 4, wherein the disorder is chronic obstructive pulmonary disease.

10. The method of claim 4, wherein the disorder is atherosclerosis.

11. The method of claim 4, wherein the disorder is restenosis.

12. A method for inhibiting the expression of VCAM-1, comprising administering an effective amount of a compound of claim 1.

13. The compound of claim 1 wherein the compound is a compound of Formula II and Y is

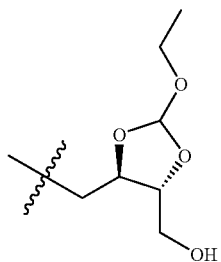

or a pharmaceutically acceptable salt or ester thereof.

14. The compound of claim 1 wherein the compound is:

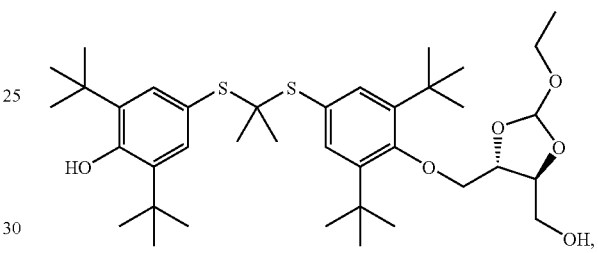

or a pharmaceutically acceptable salt or ester thereof.

15. The compound of claim 1 wherein the compound is:

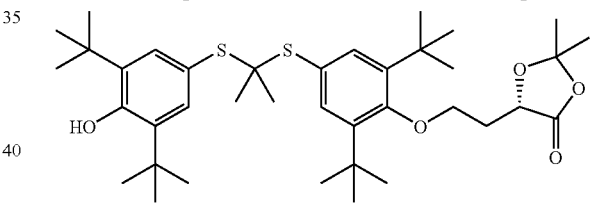

or a pharmaceutically acceptable salt or ester thereof.

16. The compound of claim 1 wherein the compound is:

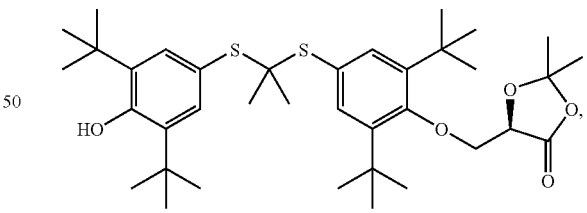

or a pharmaceutically acceptable salt or ester thereof.

17. The pharmaceutical composition of claim 3, in a form suitable for oral, parenteral, intravenous, intradermal, transdermal, subcutaneous or topical administration.

18. The pharmaceutical composition of claim 3, wherein the compound is in the form of a dosage unit.

19. The pharmaceutical composition of claim 3, wherein the dosage unit contains about 0.5–1000 mg of the compound.

20. The pharmaceutical composition of claim 3, in the form of a tablet or capsule.

21. The pharmaceutical composition of claim 3, wherein the compound is a compound of Formula II

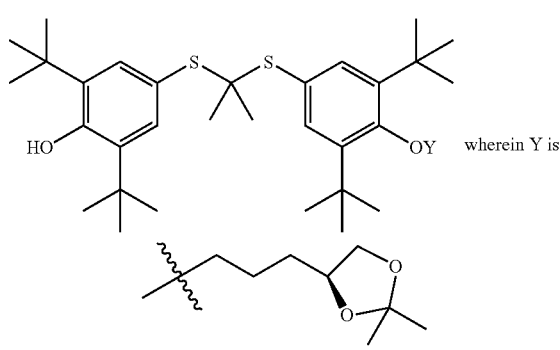 wherein Y is or a pharmaceutically acceptable salt or ester thereof.

22. The pharmaceutical composition of claim 3, wherein the compound is a compound of Formula II

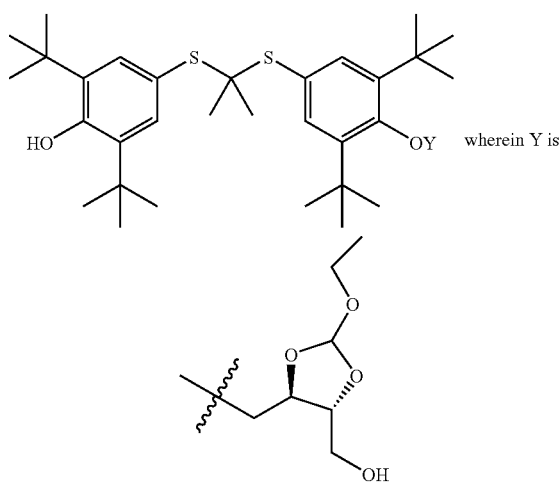 wherein Y is or a pharmaceutically acceptable salt or ester thereof.

23. The pharmaceutical composition of claim 3, wherein the compound is

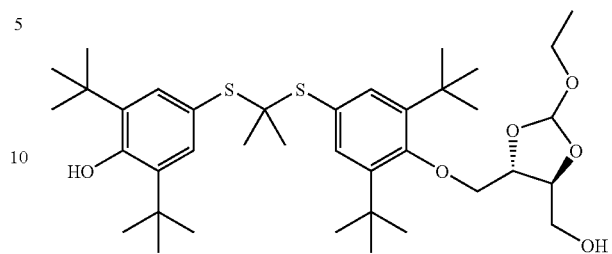

or a pharmaceutically acceptable salt or ester thereof.

24. The pharmaceutical composition of claim 3, wherein the compound is

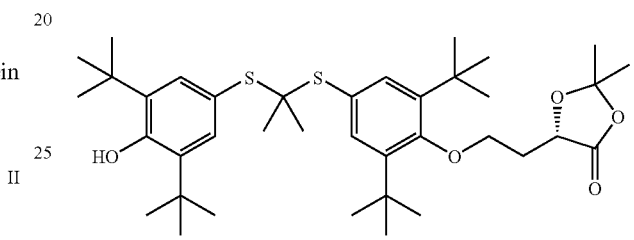

or a pharmaceutically acceptable salt or ester thereof.

25. The pharmaceutical composition of claim 3, wherein the compound is

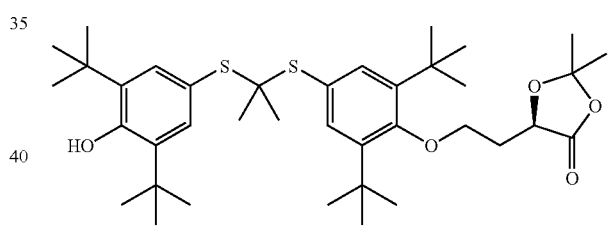

or a pharmaceutically acceptable salt or ester thereof.

* * * * *